(12) United States Patent
Chang et al.

(10) Patent No.: US 8,889,883 B2
(45) Date of Patent: Nov. 18, 2014

(54) BODIPY STRUCTURE FLUORESCENCE DYE FOR NEURAL STEM CELL PROBE

(75) Inventors: Young-Tae Chang, Singapore (SG); Seong-Wook Yun, Singapore (SG); Duanting Zhai, Singapore (SG); Kit Mun Cheryl Leong, Singapore (SG)

(73) Assignees: National University of Singapore, Singapore (SG); Agency for Science, Technology and Research, Singapore (SG)

( * ) Notice: Subject to any disclaimer, the term of this patent is extended or adjusted under 35 U.S.C. 154(b) by 0 days.

(21) Appl. No.: 13/988,734

(22) PCT Filed: Nov. 22, 2011

(86) PCT No.: PCT/SG2011/000411
§ 371 (c)(1),
(2), (4) Date: May 21, 2013

(87) PCT Pub. No.: WO2012/071012
PCT Pub. Date: May 31, 2012

(65) Prior Publication Data
US 2013/0244251 A1    Sep. 19, 2013

Related U.S. Application Data

(60) Provisional application No. 61/416,808, filed on Nov. 24, 2010.

(51) Int. Cl.
C07F 5/02     (2006.01)
C09B 57/00    (2006.01)
G01N 33/58    (2006.01)

(52) U.S. Cl.
CPC .............. *C09B 57/00* (2013.01); *G01N 33/582* (2013.01); *C07D 5/022* (2013.01)
USPC .......................................... 548/405; 435/7.1

(58) Field of Classification Search
USPC ........................................... 435/7.1; 548/405
See application file for complete search history.

(56) References Cited

U.S. PATENT DOCUMENTS

| | | | |
|---|---|---|---|
| 2005/0123563 A1 | 6/2005 | Doranz et al. | |
| 2006/0040327 A1 | 2/2006 | Amiss et al. | |
| 2006/0051833 A1 | 3/2006 | Smith et al. | |
| 2006/0275810 A1 | 12/2006 | Georges et al. | |
| 2007/0111196 A1 | 5/2007 | Alarcon et al. | |

FOREIGN PATENT DOCUMENTS

| | | |
|---|---|---|
| EP | 1754059 | 8/2010 |
| WO | WO 02/072872 A2 | 9/2002 |
| WO | WO 2008/046072 A2 | 4/2008 |
| WO | WO 2010/009015 A2 | 1/2010 |
| WO | WO 2010/035136 A2 | 4/2010 |

OTHER PUBLICATIONS

Giessler et al. "Synthesis of 3'—BODIPY-Labelled Active Esters of Nucleotides and a Chemical Primer Extension Assay on Beads" Eur. J. Org. Chem., 2010, pp. 3611-3620.*
International Search Report and Written Opinion, issued in International Application No. PCT/SG2011/000411, Title: "BODIPY Structure Fluorescence Dye for Neural Stem Cell Probe," Date of Mailing: Oct. 5, 2012.
International Preliminary Report on Patentability, issued in International Application No. PCT/SG2011/000411, Title: "BODIPY Structure Fluorescence Dye for Neural Stem Cell Probe," Date of Issuance: May 28, 2013.
Allen, J.E., et al., "Visualization and Enrichment of Live Putative Cancer Stem Cell Populations following p53 inactivation or Bax deletion using Non-Toxic Fluorescent Dyes," *Cancer Biology & Therapy*, 8(22):101-112 (Nov. 2009).
Geddes, et al., "Topics in Fluorescence Spectroscopy," vol. 9, Springer: New York, (2005).
Geddes, et al., "Topics in Fluorescence Spectroscopy", vol. 10, Springer: New York, (2005).
Okano, H., et al., "Neural Stem Cells: Involvement in Adult Neurogenesis and CNS Repair," *Philos Trans R Soc Lond B Biol Sci* 363:2111-2122, (2008).
Falk, et al., "Stage-and Area-Specific Control of Stem Cells in the Developing Nervous System," *Curr Opin Genet Dev* 19: 454-60, (2009).
Shimazaki, T., "Biology and Clinical Application of Neural Stem Cells," *Horm Res 60* Suppl 3:1-9, (2003).
Daadi, M.M, et al., "Adherent Self-Renewable Human Embryonic Stem Cell-Derived Neural Stem Cell Line: Functional Engraftment in Experimental Stroke Model," *PLOS One*, 3(2):1-9, (2008).

(Continued)

*Primary Examiner* — Joseph Kosack
(74) *Attorney, Agent, or Firm* — Hamilton, Brook, Smith & Reynolds, P.C.

(57) ABSTRACT

The present invention is directed to a fluorescence compound represented by structural Formula (I), with specificity to neural stem cells: I or a pharmaceutically acceptable salt thereof. The variables for structural Formula (I) are defined herein. Also described are methods for detection of neural stem cells, comprising using a compound of structural Formula (I) or pharmaceutically acceptable salts thereof. Compounds of structural Formula (I) can detect and separate neural stem cells without immunostaining, providing a much shorter and more convenient method for detection of neural stem cells.

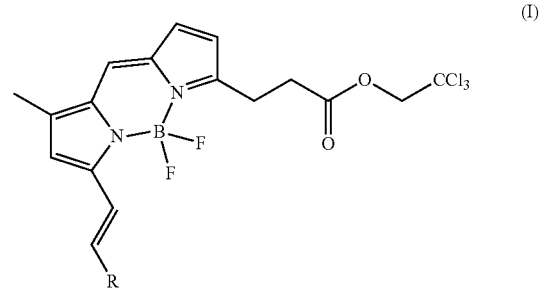

(I)

17 Claims, 10 Drawing Sheets

(56) References Cited

OTHER PUBLICATIONS

Malatesta, P., et al., "Isolation of Radial Glial Cells by Fluorescent-Activated Cell Sorting Reveals a Neuronal Lineage," *Development* 127:5253-5263, (2000).

Bibel, et al., "Differentiation of Mouse Embryonic Stem Cells into a Defined Neuronal Lineage," *Nat Neurosci* 7:1003-1009, (2004).

Malan, et al., "Fluorescent Ligands for the Histamine H2 Receptor: Synthesis and Preliminary Characterization," *Bioorg Med Chem* 12:6495-6503, (2004).

Giebler, et al., European Journal of Organic Chemistry, 19:3611-3620, (2010).

Okujima, T., "Tetrahedron", 66 (34): 6895-6900, (2010).

Kowada, T., "Organic Letters", 12(2):296-299, (2010).

Thumser, A., Molecular and Cellular Biochemistry, 299 (1-2): 67-73, (2007).

Huang, H. et al., "Liver Fatty Acid-binding Protein Taergets Fatty Acids to the Nucleus", J. Bio. Chem., 277(32): 29139-29151, (Aug. 9, 2002).

Biron-Shental, T., American J. Obstetrics and Gynecology, 197(5):516e1-516e6, (Nov. 2007).

Deng, S., et al., "Distinct Expression Levels and Patterns of Stem Cell Marker, Aldehyde, Dehydrogenase Isoform 1 (ALDH1), in Human Epithelial Cancers," *PLOS One*, 5(4):1-11, (2010).

Smith, N. W., Biochem and Biophy. Research Comm., 391(3):1455-1458, (2010).

* cited by examiner

SEQUENCE LISTING

```
<160> NUMBER OF SEQ ID NOS: 1

<210> SEQ ID NO 1
<211> LENGTH: 14
<212> TYPE: PRT
<213> ORGANISM: Mouse

<400> SEQUENCE: 1

Met Val Val Thr Leu Thr Phe Gly Asp Ile Val Ala Val Arg
1               5                   10
```

BODIPY STRUCTURE FLUORESCENCE DYE FOR NEURAL STEM CELL PROBE

RELATED APPLICATION

This application is the U.S. National Stage of International Application No. PCT/SG2011/000411, filed Nov. 22, 2011, which designates the U.S., published in English, and claims the benefit of U.S. Provisional Application No. 61/416,808, filed Nov. 24, 2010. The entire teachings of the above applications are incorporated herein by reference.

BACKGROUND OF THE INVENTION

Development of fluorescent molecules and their application are indispensable techniques for the analysis of a variety of biological phenomena. During the past few decades, a number of fluorescent small molecules have been developed as reporters and chemosensors for use in biological analyses, which typically are elaborately designed to selectively detect a target substance or conjugated to biomolecules[1]. These fluorescent molecules employ an increase or decrease in their emission intensity in response to the surrounding medium or through specific molecular recognition events. Due to their simplicity and high sensitivity, fluorescent sensors have been widely utilized as popular tools for chemical, biological and medical applications. The most general strategy for fluorescent sensor design is to combine fluorescence dye molecules with designed receptors for specific analytes, expecting that the recognition event between receptor and analyte will lead to a fluorescence property change of the dye moiety. Although many fluorescent sensors have been successfully developed through this approach, each individual development requires a major effort in both the design and synthesis of the sensors. Also, the sensor's scope of application is limited to the selected specific analytes that the sensor was rationally designed for, so-called Analyte Directed Sensors. Combinatorial dye library synthesis offers one of the most promising alternatives as Diversity Directed Sensors, once an efficient synthetic route can be developed for a diverse set of dyes.

Neural stem cells (NSC) generate the nervous system, promote neuronal plasticity and repair damage throughout life by self-renewing and differentiating into neurons and glia[2,3]. Beneficial effects of NSC engraftment into the affected brain areas in several brain diseases have been demonstrated by animal experiments[4,5]. NSC also has great potential for drug screening and efficacy testing significantly reducing the time and efforts needed in drug discovery. The conventional methods for the isolation and characterization of NSC depend on their behavior in a defined culture medium such as neurosphere formation and immunodetection of marker molecules. These methods, however, are time-dependent and involve the use of antibodies which may render the cells unsuitable for further experimental and therapeutic applications. Therefore, a need exists to develop novel chemical compounds that are useful for detection of neural stem cells.

SUMMARY OF THE INVENTION

A novel chemical structure with fluorescence emission and specificity to neural stem cells is described. This scaffold is compatible with a range of chemical functional groups, and can be bioconjugated to proteins as well as other macromolecules of interest, such as carbohydrates and lipids. One of the compounds, named as compound of designation (CDr3), selectively stains both human and mouse neural stem cells (NSC) by binding to a NSC marker protein fatty acid binding protein 7 (FABP7).

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

DETAILED DESCRIPTION OF THE INVENTION

Figure 1:
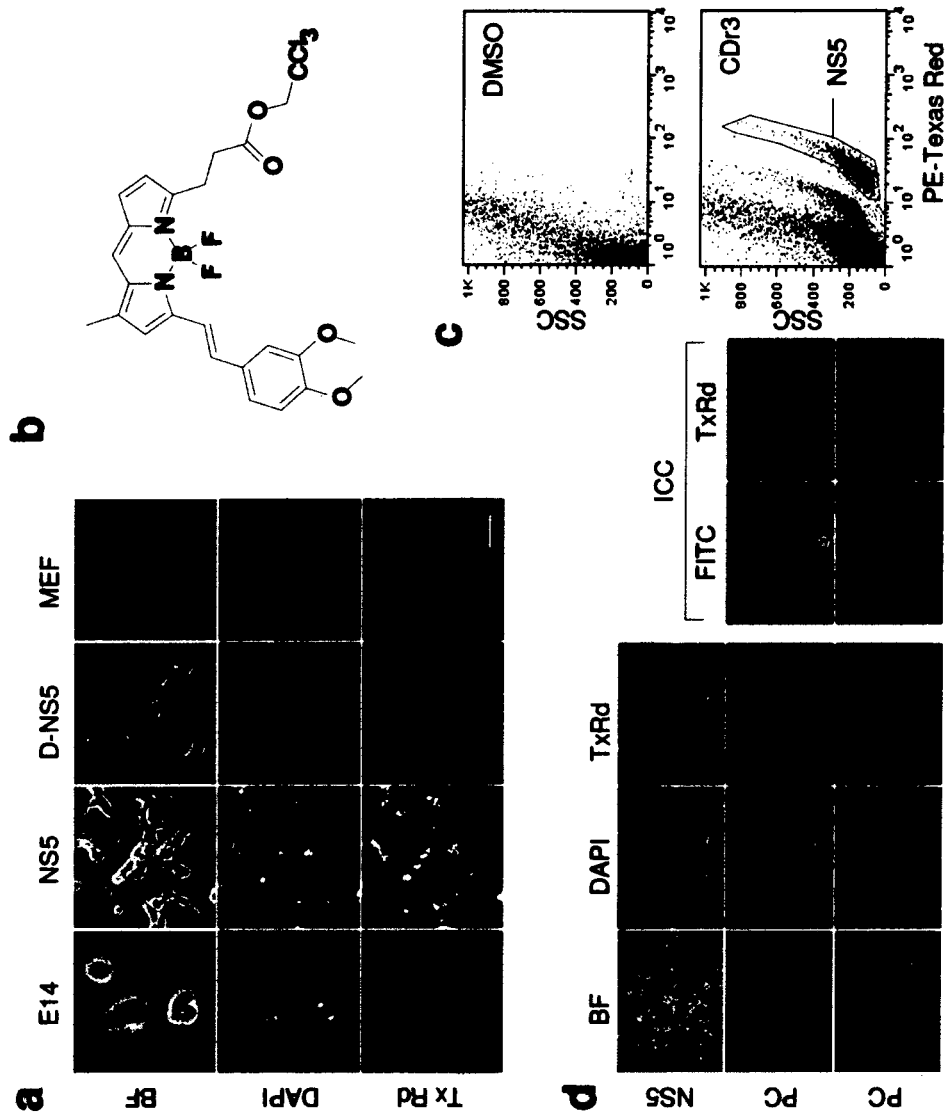
FIG. 1A shows the selective staining of NS5 by CDr3. Nuclei of all E14, NS5, D-NS5 and MEF were visualized by Hoechst 33342 (DAPI); but only NS5 was selectively stained by CDr3 (TxRd). Top panel, bright field (BF) images; middle and bottom panels, fluorescent images obtained with DAPI and Texas Red filter set. Scale bar, 50 µm.
FIG. 1B shows the chemical structure of CDr3.
FIG. 1C shows the flow cytometry dot plot images of E14, NS5, D-NS5 and MEF incubated with CDr3. DMSO was added for unstained control cells. The images of each type of cells were overlaid. Segregated NS5 cells by CDr3 are marked.
FIG. 1D shows selective staining of NS5 by CDr3. Mixed primary mouse brain cells (PC) cultured for 2 weeks in vitro were incubated with CDr3 and Hoechst 33342. The images of living cells are shown in bright field (BF) and fluorescence (DAPI and Texas Red) panels. The primary brain cells with various morphologies were not stained by CDr3, while NS5 treated in parallel was stained. The images of the same cells were acquired after immunocytochemical staining (ICC) with antibodies to neuron-specific class III β-tubulin (Tuj1; TxRd channel) and astrocyte-specific glial fibrillary acidic protein (GFAP; FITC channel). Scale bar, 100 µm.

The teachings of all patents, published applications and references cited herein are incorporated by reference in their entirety.

The invention pertains to a novel chemical structure with fluorescence emission and specificity to neural stem cells. This scaffold is compatible with a range of chemical functional groups, and can be bioconjugated to proteins as well as other macromolecules of interest, such as carbohydrates and lipids. One of the compounds, named as compound of designation (CDr3), selectively stains both human and mouse neural stem cells (NSC) by binding to a NSC marker protein fatty acid binding protein 7 (FABP7).

One embodiment of the invention is a compound represented by structural Formula (I) or pharmaceutically acceptable salts thereof:

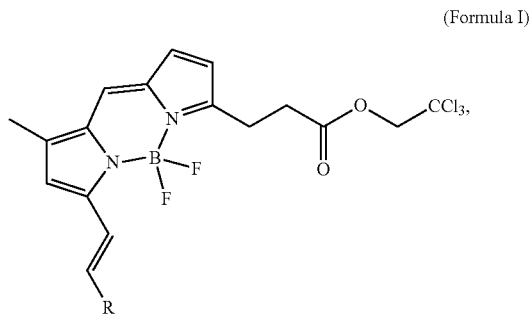

(Formula I)

wherein:
R is $(C_6-C_{10})$aryl, $(C_5-C_{10})$heteroaryl, $(C_6-C_{10})$aryl$(C_2-C_6)$alkenyl or 2-4 member polycyclyl, wherein each 2-4 member polycyclyl optionally and independently contains 1-2 ring heteroatoms selected from oxygen, nitrogen and sulfur;
and wherein R is optionally substituted with 1-4 substituents independently selected from $(C_1-C_6)$alkyl, halo$(C_1-C_6)$alkyl, hydroxy$(C_0-C_6)$alkyl, $(C_6-C_{10})$aryl, halo $(C_6-C_{10})$aryl, hydroxy$(C_6-C_{10})$aryl, $(C_1-C_6)$alkoxy, halo$(C_1-C_6)$alkoxy, $(C_3-C_8)$cycloalkyl, halo$(C_6-C_{10})$aryl$(C_1-C_6)$alkoxy, halogen, amino, $(C_1-C_6)$alkoxy$(C_6-C_{10})$aryl$(C_1-C_6)$alkoxy, nitro, (3 to 9 membered)heterocyclyl, $(C_0-C_6)$alkyl$(C_6-C_{10})$aryl$(C_0-C_6)$alkoxy, $(C_5-C_{10})$heterocycle, —OCF$_3$, —B(OH)$_2$, cyano$(C_1-C_6)$alkylene amino, $(C_1-C_6)$alkoxyamino, $(C_6-C_{10})$aryl$(C_2-C_6)$alkenyl, $(C_2-C_6)$alkenyl$(C_1-C_6)$alkoxy, $(C_1-C_6)$sulfoxy or —N(CH$_3$)(C$_1$-C$_6$)OH.

Another embodiment of the invention is a method for detection of a neural stem cell (NSC) comprising:
a) staining said neural stem cell with a compound, forming a dye-stained neural stem cell by binding said compound to a marker protein of said neural stem cell, wherein said compound is of structural Formula (I) or pharmaceutically acceptable salts thereof:
b) optionally incubating product of step a) to form a said incubated dye-stained stem (intensity of fluorescence can be increased by incubation for the period of time sufficient for achieving desired intensity, e.g., from about 1 hour to about 24 hours, but less or more time may be acceptable.);
c) analyzing said incubated dye-stained stem cell by a flow cytometry and FACS; and
d) subjecting said dye-stained neural stem cell to two-dimensional SDS-PAGE (2DE) fluorescence scanning to detect fluorescence signal, wherein the presence of a signal is indicative of the presence of said neural stem cell.

In one embodiment of the invention said method is applied in neural stem cell biology and regenerative medicine.

Scheme 1. General synthetic scheme.

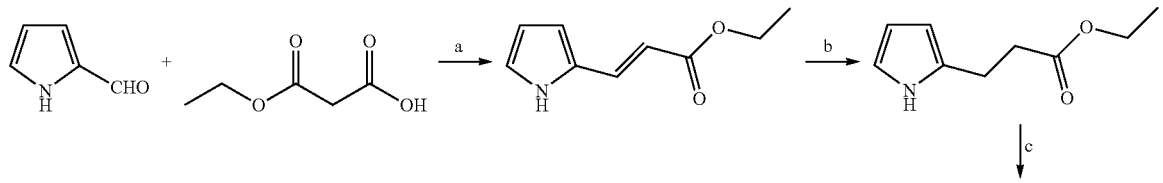

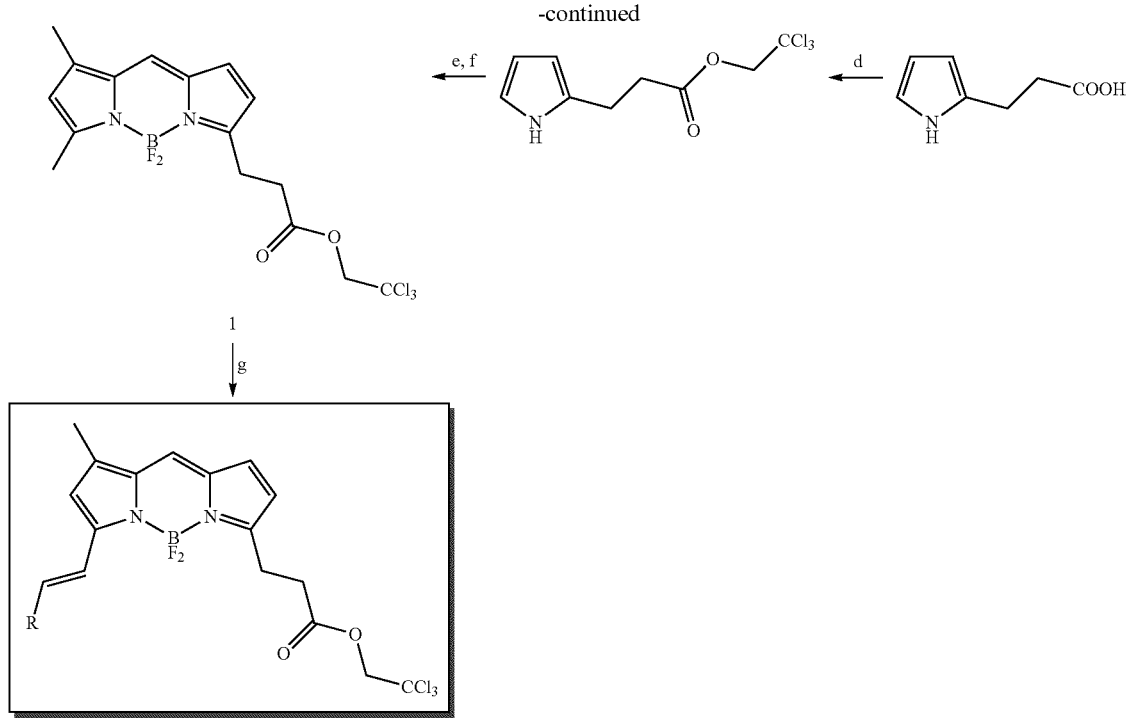

(a) pyridine, piperidine, 50° C., 48 h, then 80° C., 24 h, (b) H$_2$, Pd/C, MeOH, RT, 6 h, (c) K$_2$CO$_3$, H$_2$O/EtOH, reflux, overnight, (d) 2,2,2-trichloroethanol, pyridine, DCC, EA, RT, overnight, (e) 3,5-dimethyl-1H-pyrrole-2-carbaldehyde, POCl$_3$, DCM, RT, 4 h, (f) DIEA, BF$_3$OEt$_2$, DCM, RT, overnight, (g) R—CHO, pyrrolidine, acetic acid, ACN, 85° C., 15 min.

CHART 1

Building block acid chlorides employed in the synthesis (R—CHO in Scheme 1).

| Code | Structure |
|------|-----------|
| 1 | 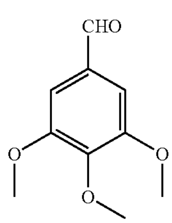 |
| 2 | 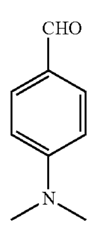 |

CHART 1-continued

Building block acid chlorides employed in the synthesis (R—CHO in Scheme 1).

| Code | Structure |
|------|-----------|
| 3 | 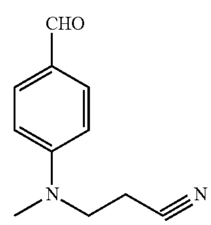 |
| 4 | 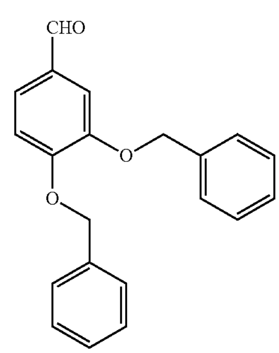 [SMILES: O=Cc1ccc(OCc2ccccc2)c(OCc2ccccc2)c1] |

CHART 1-continued
Building block acid chlorides employed in the synthesis (R—CHO in Scheme 1).
| Code | Structure |
|---|---|
| 5 | 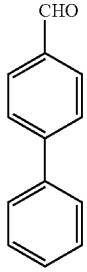 [SMILES: O=Cc1ccc(-c2ccccc2)cc1] |
| 6 | 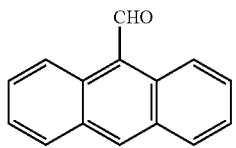 [SMILES: O=Cc1c2ccccc2cc2ccccc12] |
| 7 | 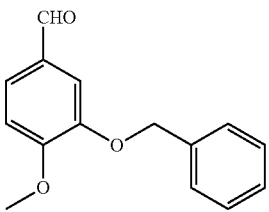 [SMILES: COc1ccc(C=O)cc1OCc1ccccc1] |
| 9 | 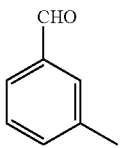 |
| 14 | 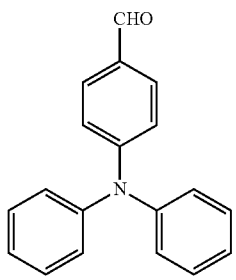 [SMILES: O=Cc1ccc(N(c2ccccc2)c2ccccc2)cc1] |
| 16 | 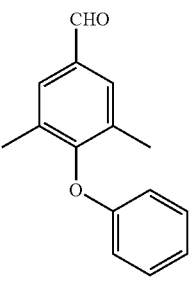 [SMILES: Cc1cc(C=O)cc(C)c1Oc1ccccc1] |
| 17 | 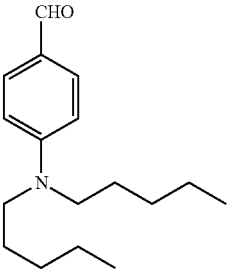 [SMILES: CCCCCN(CCCCC)c1ccc(C=O)cc1] |
| 18 | 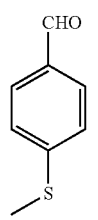 |
| 19 | 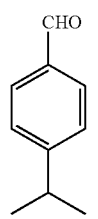 |
| 20 | 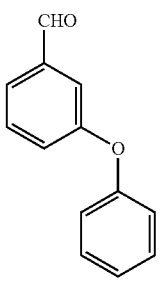 [SMILES: O=Cc1cccc(Oc2ccccc2)c1] |
| 22 | 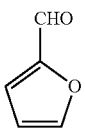 |
| 25 | 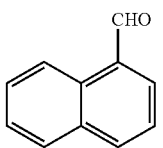 [SMILES: O=Cc1cccc2ccccc12] |
| 26 | 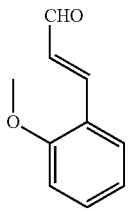 |

CHART 1-continued

Building block acid chlorides employed in the synthesis
(R—CHO in Scheme 1).

| Code | Structure |
|------|-----------|
| 30 | 5-(thiophen-2-yl)thiophene-2-carbaldehyde |
| 32 | 4-methoxynaphthalene-1-carbaldehyde |
| 33 | 2-hydroxy-4-methylbenzaldehyde |
| 34 | 2-methylnaphthalene-1-carbaldehyde |
| 36 | 4-methylnaphthalene-1-carbaldehyde |
| 37 | benzo[b]thiophene-3-carbaldehyde |
| 38 | 2-chloro-3-hydroxy-4-methoxybenzaldehyde |
| 40 | [1,1'-biphenyl]-2-carbaldehyde |
| 42 | 3-(4-methoxyphenoxy)benzaldehyde |
| 43 | 5-tert-butyl-2-hydroxybenzaldehyde |
| 45 | 4-pentyloxybenzaldehyde |
| 46 | 4-butoxybenzaldehyde |
| 48 | 4-(prop-2-yn-1-yloxy)benzaldehyde |
| 52 | 4-((4-bromobenzyl)oxy)benzaldehyde |

CHART 1-continued

Building block acid chlorides employed in the synthesis (R—CHO in Scheme 1).

| Code | Structure |
|------|-----------|
| 53 | 3,4-diethoxybenzaldehyde |
| 54 | 5-bromo-2-methoxybenzaldehyde |
| 61 | 2-methoxy-1-naphthaldehyde |
| 62 | 3,4-dimethoxybenzaldehyde |
| 63 | 4-ethoxy-3-methoxybenzaldehyde |
| 65 | 5-phenylthiophene-2-carbaldehyde |
| 67 | 2,3,4,5-tetramethylbenzaldehyde |
| 68 | 4-(trifluoromethoxy)benzaldehyde |
| 69 | (E)-4-styrylbenzaldehyde |
| 70 | 5,7-dimethoxy-1-naphthaldehyde |
| 73 | 5-bromo-2-hydroxybenzaldehyde |
| 76 | 9H-fluorene-2-carbaldehyde |
| 77 | 4-propylbenzaldehyde |

CHART 1-continued

Building block acid chlorides employed in the synthesis
(R—CHO in Scheme 1).

| Code | Structure |
|---|---|
| 82 | 2,4,6-trimethoxybenzaldehyde |
| 83 | 2,3-dimethoxybenzaldehyde |
| 88 | 4-(pyridin-2-yl)benzaldehyde |
| 89 | acenaphthene-5-carbaldehyde |
| 90 | 4-(benzyloxy)benzaldehyde |
| 91 | 4-[(2-hydroxyethyl)(methyl)amino]benzaldehyde |
| 94 | 1-methyl-1H-indole-3-carbaldehyde |
| 95 | 4-hydroxy-3,5-dimethoxybenzaldehyde |
| 97 | 2-hydroxy-3-methoxybenzaldehyde |
| 98 | 3,5-di-tert-butyl-2-hydroxybenzaldehyde |
| 101 | 4-phenoxybenzaldehyde |
| 103 | pyrene-1-carbaldehyde |
| 105 | 3-hydroxybenzaldehyde |

CHART 1-continued

Building block acid chlorides employed in the synthesis
(R—CHO in Scheme 1).

| Code | Structure |
|------|-----------|
| 107 | 4-(diethylamino)benzaldehyde |
| 108 | 2,4,6-trimethylbenzaldehyde |
| 110 | 4-methoxybenzaldehyde |
| 121 | 5-chloro-2-hydroxybenzaldehyde |
| 126 | 3-ethoxy-2-hydroxybenzaldehyde |
| 132 | 3-hydroxy-4-methoxybenzaldehyde |
| 135 | 5-methylfuran-2-carbaldehyde |
| 136 | 1-methyl-1H-pyrrole-2-carbaldehyde |
| 137 | 2-naphthaldehyde |
| 139 | benzo[d][1,3]dioxole-5-carbaldehyde |
| 140 | 4-propoxybenzaldehyde |
| 144 | 2,4,5-trimethoxybenzaldehyde |
| 153 | 4-hydroxybenzaldehyde |
| 163 | 4-(3-(dimethylamino)propoxy)benzaldehyde |

CHART 1-continued

Building block acid chlorides employed in the synthesis
(R—CHO in Scheme 1).

| Code | Structure |
|------|-----------|
| 164 | 3-ethoxy-4-methoxybenzaldehyde |
| 177 | 4-tert-butylbenzaldehyde |
| 178 | 4-(4-methoxyphenoxy)benzaldehyde |
| 186 | 3-methoxybenzaldehyde |
| 187 | 4-formylphenylboronic acid |
| 190 | 2-hydroxybenzaldehyde |
| 195 | 5-(3-chloro-4-methoxyphenyl)furan-2-carbaldehyde |
| 199 | 4-(pyrimidin-5-yl)benzaldehyde |
| 206 | 2,4-dimethoxybenzaldehyde |
| 209 | 3,5-dimethoxybenzaldehyde |
| 216 | 3,4-dimethylbenzaldehyde |
| 223 | 2-(benzyloxy)-4,5-dimethoxybenzaldehyde |

CHART 1-continued

Building block acid chlorides employed in the synthesis (R—CHO in Scheme 1).

| Code | Structure |
|------|-----------|
| 228 | 5-bromo-2,3-dimethoxybenzaldehyde |
| 236 | 5-methylthiophene-2-carbaldehyde |
| 238 | 5-(hydroxymethyl)furan-2-carbaldehyde |
| 241 | 3,5-dibromo-2-methoxybenzaldehyde |
| 242 | 3-iodo-4,5-dimethoxybenzaldehyde |
| 243 | 2,6-dimethylbenzaldehyde |
| 245 | 2-fluoro-5-methoxybenzaldehyde |
| 247 | 5-bromo-2,4-dimethoxybenzaldehyde |
| 251 | 2-ethylbenzaldehyde |
| 257 | 4-(bis(2-hydroxyethyl)amino)benzaldehyde |
| 259 | 3-bromo-4,5-dimethoxybenzaldehyde |
| 260 | 3-bromo-4-methoxybenzaldehyde |
| 263 | 4-butylbenzaldehyde |
| 264 | 6-bromobenzo[d][1,3]dioxole-5-carbaldehyde |
| 268 | 4-(2-bromoethoxy)-3-methoxybenzaldehyde |

CHART 1-continued

Building block acid chlorides employed in the synthesis
(R—CHO in Scheme 1).

| Code | Structure |
|------|-----------|
| 274 | 3-chloro-4-methoxybenzaldehyde |
| 282 | 5-chloro-2,3-dimethoxybenzaldehyde |
| 284 | 5-(3-chlorophenyl)furan-2-carbaldehyde |
| 290 | 4-(3-chlorophenoxy)benzaldehyde |
| 298 | 4-(3-methoxyphenoxy)benzaldehyde |
| 299 | 4-(3,4-dichlorophenoxy)benzaldehyde |
| 300 | 4-(4-methylphenoxy)benzaldehyde |
| 301 | 2,3-dimethoxynaphthalene-1-carbaldehyde |
| 305 | 2-fluoro-4,5-dimethoxybenzaldehyde |
| 307 | 3-hydroxy-4,5-dimethoxybenzaldehyde |
| 308 | 4-(3,5-dichlorophenoxy)benzaldehyde |

CHART 1-continued

Building block acid chlorides employed in the synthesis (R—CHO in Scheme 1).

| Code | Structure |
|---|---|
| 310 | 4-methoxy-2,3-dimethylbenzaldehyde |
| 311 | 4-fluoro-3-phenoxybenzaldehyde |
| 313 | 4-hydroxy-3-methylbenzaldehyde |
| 314 | 3-fluoro-4-methoxybenzaldehyde |
| 316 | 2,4-diethoxybenzaldehyde |
| 319 | 5-phenylfuran-2-carbaldehyde |
| 320 | 2-ethoxy-3-methoxybenzaldehyde |
| 322 | 4-(4-fluorophenoxy)benzaldehyde |
| 323 | 4-(ethoxymethyl)benzaldehyde |
| 325 | 3,5-di-tert-butyl-2-methoxybenzaldehyde |
| 329 | 4-fluoro-3-methoxybenzaldehyde |
| 331 | 3,5-bis(benzyloxy)benzaldehyde |

CHART 1-continued

Building block acid chlorides employed in the synthesis
(R—CHO in Scheme 1).

| Code | Structure |
|---|---|
| 332 | 2,2-difluoro-benzo[1,3]dioxole-5-carbaldehyde |
| 335 | 4-methoxy-3-methylbenzaldehyde |
| 340 | 10-methylanthracene-9-carbaldehyde |
| 343 | 2,4,5-trimethylbenzaldehyde |
| 347 | 2,4-dimethoxy-3-methylbenzaldehyde |
| 349 | 2,3-dimethylbenzaldehyde |
| 351 | 4-methoxy-2-methylbenzaldehyde |
| 357 | 2-nitro-3-(pyrrolidin-1-yl)benzaldehyde |
| 359 | 2-fluoro-4-methoxybenzaldehyde |
| 361 | 3,5-dimethylbenzaldehyde |
| 366 | 2-hydroxy-4,6-dimethoxybenzaldehyde |
| 369 | thiophene-3-carbaldehyde |
| 370 | 2,4-dimethylbenzaldehyde |
| 371 | 5-(4-chlorophenyl)furan-2-carbaldehyde |

CHART 1-continued

Building block acid chlorides employed in the synthesis (R—CHO in Scheme 1).

| Code | Structure |
|------|-----------|
| 377 | 4-(dimethylamino)-1-naphthaldehyde |
| 378 | 4-[(4-fluorobenzyl)oxy]benzaldehyde |
| 383 | 4,5-dimethylthiophene-2-carbaldehyde |
| 393 | 5-(2-chlorophenyl)furan-2-carbaldehyde |
| 397 | 3-ethoxy-4-hydroxybenzaldehyde |
| 403 | (E)-2-methyl-3-phenylacrylaldehyde |
| 423 | thiophene-2-carbaldehyde |
| 428 | 5-(4-bromophenyl)furan-2-carbaldehyde |
| 429 | 4-ethoxybenzaldehyde |
| 435 | 4-[4-(tert-butyl)phenoxy]benzaldehyde |
| 441 | 9-ethyl-9H-carbazole-3-carbaldehyde |
| 473 | 4-hydroxy-2-methoxybenzaldehyde |
| 474 | 2,5-dimethylbenzaldehyde |

CHART 1-continued

Building block acid chlorides employed in the synthesis
(R—CHO in Scheme 1).

| Code | Structure |
|---|---|
| 480 | 2,6-dimethoxybenzaldehyde |
| 483 | 4-benzyloxy-3-methoxybenzaldehyde |
| 485 | 3-benzyloxybenzaldehyde |
| 486 | 2,3-dihydro-1,4-benzodioxine-6-carbaldehyde |
| 487 | 2-bromo-4,5-dimethoxybenzaldehyde |
| 489 | 4-ethylbenzaldehyde |
| 490 | 2,3,4-trimethoxybenzaldehyde |
| 495 | 6-methoxy-2-naphthaldehyde |
| 496 | 4-hydroxy-3-methoxybenzaldehyde (vanillin) |
| 498 | 4-morpholinobenzaldehyde |
| 499 | 4-(piperidin-1-yl)benzaldehyde |
| 501 | 4-(pyrrolidin-1-yl)benzaldehyde |

DEFINITIONS

"Alkyl" means a saturated aliphatic branched or straight-chain monovalent hydrocarbon radical having the specified number of carbon atoms. Thus, "($C_1$-$C_6$) alkyl" means a radical having from 1-6 carbon atoms in a linear or branched arrangement. "($C_1$-$C_6$)alkyl" includes methyl, ethyl, propyl, butyl, pentyl and hexyl.

"Alkylene" means a saturated aliphatic straight-chain divalent hydrocarbon radical having the specified number of carbon atoms. Thus, "($C_1$-$C_6$)alkylene" means a divalent saturated aliphatic radical having from 1-6 carbon atoms in a linear arrangement. "($C_1$-$C_6$)alkylene" includes methylene, ethylene, propylene, butylene, pentylene and hexylene.

"Heterocycle" means a saturated or partially unsaturated (4-7 membered) monocyclic heterocyclic ring containing one nitrogen atom and optionally 1 additional heteroatom independently selected from N, O or S. When one heteroatom is S, it can be optionally mono- or di-oxygenated (i.e., —S(O)— or —S(O)$_2$—). Examples of monocyclic heterocycle include, but not limited to, azetidine, pyrrolidine, piperidine, piperazine, hexahydropyrimidine, tetrahydropyran, tetrahydropyran, morpholine, thiomorpholine, thiomorpholine 1,1-dioxide, tetrahydro-2H-1,2-thiazine, tetrahydro-2H-1,2-thiazine 1,1-dioxide, isothiazolidine, or isothiazolidine 1,1-dioxide.

"Cycloalkyl" means saturated aliphatic cyclic hydrocarbon ring. Thus, "$C_3$-$C_7$ cycloalkyl" means (3-7 membered) saturated aliphatic cyclic hydrocarbon ring. $C_3$-$C_7$ cycloalkyl includes, but is not limited to cyclopropyl, cyclobutyl, cyclopentyl, cyclohexyl and cycloheptyl.

The term "alkoxy" means —O-alkyl; "hydroxyalkyl" means alkyl substituted with hydroxy; "aralkyl" means alkyl substituted with an aryl group; "alkoxyalkyl" mean alkyl substituted with an alkoxy group; "alkylamine" means amine substituted with an alkyl group; "cycloalkylalkyl" means alkyl substituted with cycloalkyl; "dialkylamine" means amine substituted with two alkyl groups; "alkylcarbonyl" means —C(O)-A*, wherein A* is alkyl; "alkoxycarbonyl" means —C(O)—OA*, wherein A* is alkyl; and where alkyl is as defined above and includes methoxy, ethoxy, propoxy, butoxy, pentoxy and hexoxy.

"Cycloalkoxy" means an cycloalkyl-O— group wherein the cycloalkyl is as defined above. Exemplary ($C_3$-$C_7$)cycloalkyloxy groups include cyclopropoxy, cyclobutoxy, cyclopentoxy, cyclohexoxy and cycloheptoxy.

Haloalkyl and halocycloalkyl include mono, poly, and perhaloalkyl groups where each halogen is independently selected from fluorine, chlorine, and bromine.

"Hetero" refers to the replacement of at least one carbon atom member in a ring system with at least one heteroatom selected from N, S, and O. A hetero ring system may have 1 or 2 carbon atom members replaced by a heteroatom.

"Halogen" and "halo" are interchangeably used herein and each refers to fluorine, chlorine, bromine, or iodine.

"Cyano" means —C≡N.

"Nitro" means —NO$_2$.

As used herein, an amino group may be a primary (—NH$_2$), secondary (—NHR$_x$), or tertiary (—NR$_x$R$_y$), wherein R$_x$ and R$_y$ may be any of the optionally substituted alkyls described above.

The terms "haloalkyl" and "haloalkoxy" mean alkyl or alkoxy, as the case may be, substituted with one or more halogen atoms. The term "halogen" means F, Cl, Br or I. Preferably the halogen in a haloalkyl or haloalkoxy is F.

The term "acyl group" means —C(O)B*, wherein B* is an optionally substituted alkyl group or aryl group (e.g., optionally substituted phenyl).

An "alkylene group" is represented by —[CH$_2$]$_z$—, wherein z is a positive integer, preferably from one to eight, more preferably from one to four.

An "alkenylene group" is an alkylene in which at least a pair of adjacent methylenes are replaced with —CH=CH—.

The term "(C6-C10)aryl" used alone or as part of a larger moiety as in "arylalkyl", "arylalkoxy", or "aryloxyalkyl", means carbocyclic aromatic rings. The term "carbocyclic aromatic group" may be used interchangeably with the terms "aryl", "aryl ring" "carbocyclic aromatic ring", "aryl group" and "carbocyclic aromatic group". An aryl group typically has 6-14 ring atoms. A "substituted aryl group" is substituted at any one or more substitutable ring atom. The term "$C_{6-14}$ aryl" as used herein means a monocyclic, bicyclic or tricyclic carbocyclic ring system containing from 6 to 14 carbon atoms and includes phenyl, naphthyl, anthracenyl, 1,2-dihydronaphthyl, 1,2,3,4-tetrahydronaphthyl, fluorenyl, indanyl, indenyl and the like.

The term "heteroaryl", "heteroaromatic", "heteroaryl ring", "heteroaryl group" and "heteroaromatic group", used alone or as part of a larger moiety as in "heteroarylalkyl" or "heteroarylalkoxy", refers to aromatic ring groups having five to fourteen ring atoms selected from carbon and at least one (typically 1-4, more typically 1 or 2) heteroatoms (e.g., oxygen, nitrogen or sulfur). They include monocyclic rings and polycyclic rings in which a monocyclic heteroaromatic ring is fused to one or more other carbocyclic aromatic or heteroaromatic rings. The term "5-14 membered heteroaryl" as used herein means a monocyclic, bicyclic or tricyclic ring system containing one or two aromatic rings and from 5 to 14 atoms of which, unless otherwise specified, one, two, three, four or five are heteroatoms independently selected from N, NH, N($C_{1-6}$alkyl), O and S.

The term "2-4 member polycyclyl is a cyclic compound with 2-4 hydrocarbon loop or ring structures (e.g., benzene rings). The term generally includes all polycyclic aromatic compounds, including the polycyclic aromatic hydrocarbons, the heterocyclic aromatic compounds containing sulfur, nitrogen, oxygen, or another non-carbon atoms, and substituted derivatives of these.

The term "Alkenyl" means a straight or branched hydrocarbon radical having a specified number of carbon atoms and includes at least one double bond. The ($C_6$-$C_{10}$)aryl($C_2$-$C_6$) alkenyl group connects to the remainder of the molecule through the ($C_2$-$C_6$)alkenyl portion of ($C_6$-$C_{10}$)aryl($C_2$-$C_6$) alkenyl.

Another embodiment of the present invention is a pharmaceutical composition comprising one or more pharmaceutically acceptable carrier and/or diluent and a compound disclosed herein or a pharmaceutically acceptable salt thereof.

"Pharmaceutically acceptable carrier" and "pharmaceutically acceptable diluent" means non-therapeutic components that are of sufficient purity and quality for use in the formulation of a composition of the invention that, when appropriately administered to an animal or human, typically do not produce an adverse reaction, and that are used as a vehicle for a drug substance (i.e. a compound of the present invention).

Pharmaceutically acceptable salts of the compounds of the present invention are also included. For example, an acid salt of a compound of the present invention containing an amine or other basic group can be obtained by reacting the compound with a suitable organic or inorganic acid, resulting in pharmaceutically acceptable anionic salt forms. Examples of anionic salts include the acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, mandelate, mesylate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate, and triethiodide salts.

Salts of the compounds of the present invention containing a carboxylic acid or other acidic functional group can be prepared by reacting with a suitable base. Such a pharmaceutically acceptable salt may be made with a base which affords a pharmaceutically acceptable cation, which includes alkali metal salts (especially sodium and potassium), alkaline earth metal salts (especially calcium and magnesium), aluminum salts and ammonium salts, as well as salts made from physiologically acceptable organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, dehydroabietylamine, N,N'-bisdehydroabietylamine, glucamine, N-methylglucamine, collidine, quinine, quinoline, and basic amino acids such as lysine and arginine.

EXAMPLES 4,4-Difluoro-4-bora-3a,4a-diaza-s-indacene (BODIPY) has superior advantages to be one of the more versatile fluorophores, such as high quantum yield, tunable fluorescence characteristics, high photo stability, and narrow emission bandwidth. Since the first discovery of BODIPY dyes in 1968, chemical modification for BODIPY scaffold has been well explored. Thus great numbers of BODIPY dyes have been used to label biomolecules. A large numbers of sensors and markers based on BODIPY scaffold have also been developed. But BODIPY-based library synthesis has been rarely reported due to the synthetic challenge.

Here we disclose our invention of a novel diversity oriented fluorescence BODIPY active ester compound library synthesized via solution phase synthetic method and one of the compounds which has been identified as neural stem cell selective imaging probe.

To develop fluorescent imaging probes which selectively detect NSC, we have screened in-house-generated 3,160 Diversity Oriented Fluorescence Library (DOFL) compounds in E14 mouse embryonic stem cell (mESC), E14-derived NS5 NSC, differentiated NS5 into astrocyte (D-NS5) and mouse embryonic fibroblast (MEF). For high throughput screening, the 4 different types of cells were prepared side by side in 384-well plates and incubated with 0.5 or 1.0 μM of compounds. After 24 hr incubation, the bright field and fluorescence images of the cells were acquired on an automated imaging microscope system ImageXpress Micro™ and the fluorescence intensity of the stained cells was analyzed using MetaXpress® image processing software. Through the followed secondary and tertiary screenings CDr3 has been identified as the hit molecule that stains NS5 most selectively and brightly (FIG. 1).

The intrinsic fluorescence property of our compounds makes it possible to track the target without any modification from the stained living cells through all processes for identification once it binds strongly to the target molecules. When we subjected CDr3-stained NS5 lysate to two-dimensional sodium dodecyl sulfate polyacrylamide gel electrophoresis (SDS-PAGE (2DE)) for a fluorescence scanning, a major spot of approximately 15 kDa was detected (FIG. 2A).

Figure 2:
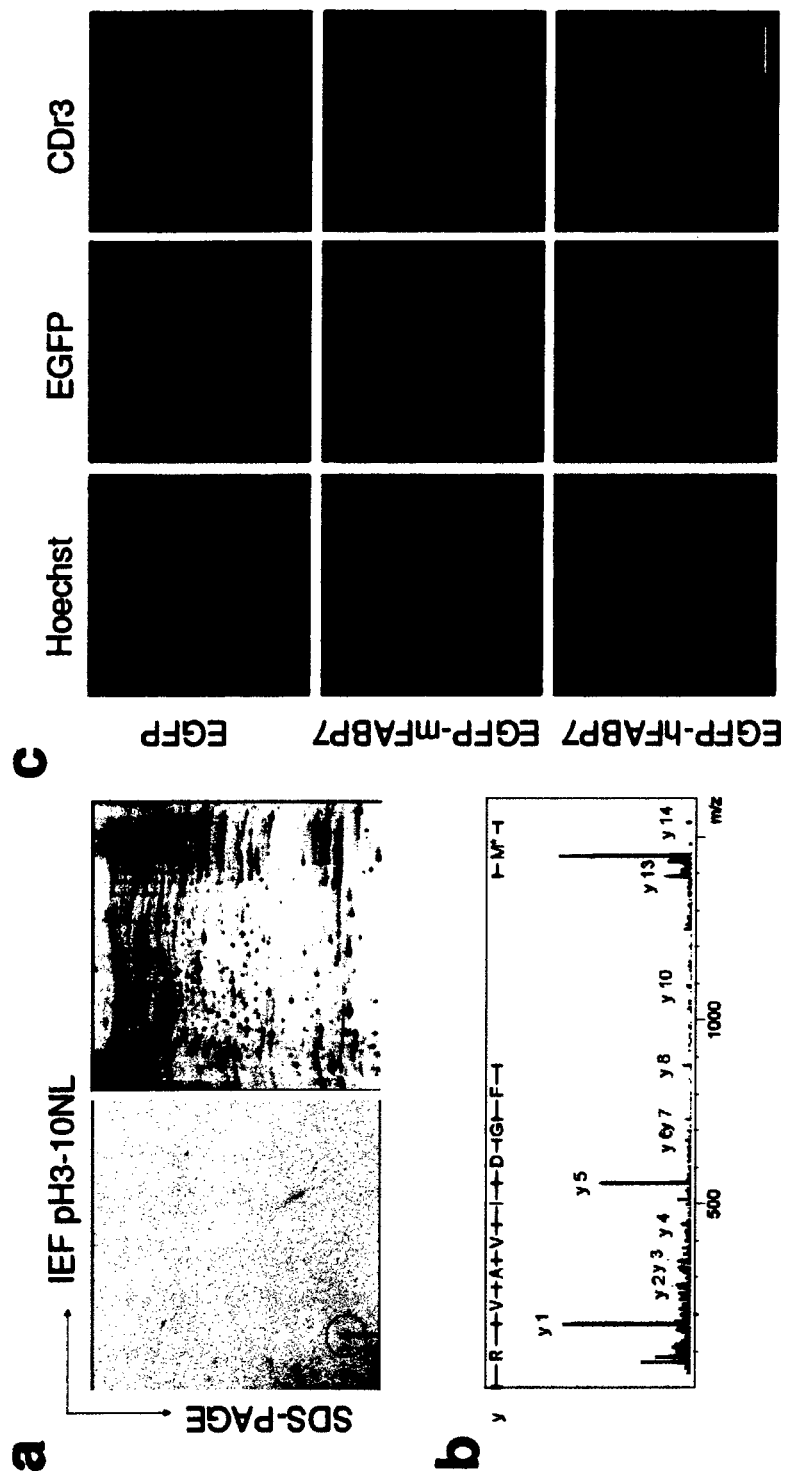
FIG. 2A shows the identification of CDr3 binding protein. A protein lysate of CDr3-stained NS5 was separated by 2DE. The major fluorescent spot was marked with a circle (left panel). Many silver-stained protein spots were detected in a duplicate gel (right panel).
FIG. 2B shows the MS/MS fragment ion analysis of tryptic peptide (MVVTLTFGDIVAVR) SEQ ID No.: 1, indicated FABP7 as a binding target of CDr3. Only the main y-series of ion fragmentation was labeled in the spectrum. M* indicates oxidation at methionine residue.
FIG. 2C shows the fluorescence signals from EGFP and CDr3 overlap only in the cells expressing either mouse FABP7 or human FABP7 fused to EGFP. The fluorescence images were acquired on a Nikon Ti microscope using DAPI (Hoechst), FITC (EGFP) and Texas Red (Cdr3) filter sets. Scale bar, 50 µm.

Matrix-assisted laser desorption/ionization-time of flight/time of flight mass spectrometry (MALDI-TOF/TOF MS) and MS/MS analysis allowed us to identify the protein spot as FABP7 (FIG. 2B). Among the currently known 9 mammalian FABPs that play pivotal roles in transporting and trafficking of lipids in various tissues, FABP7 is particularly expressed in the central nervous system and a well-known marker of radial glial cells which play as NSC in the brain[6]. To confirm that FABP7 is the specific binding target of CDr3, we cloned both human and mouse FABP7 genes and fused them to EGFP constructs for expression in HEK293 cells. We incubated the cells with CDr3 and observed the signals of EGFP and CDr3 overlap in the cells that express either human or mouse FABP7 fused to EGFP (FIG. 2C).

Figure 3:
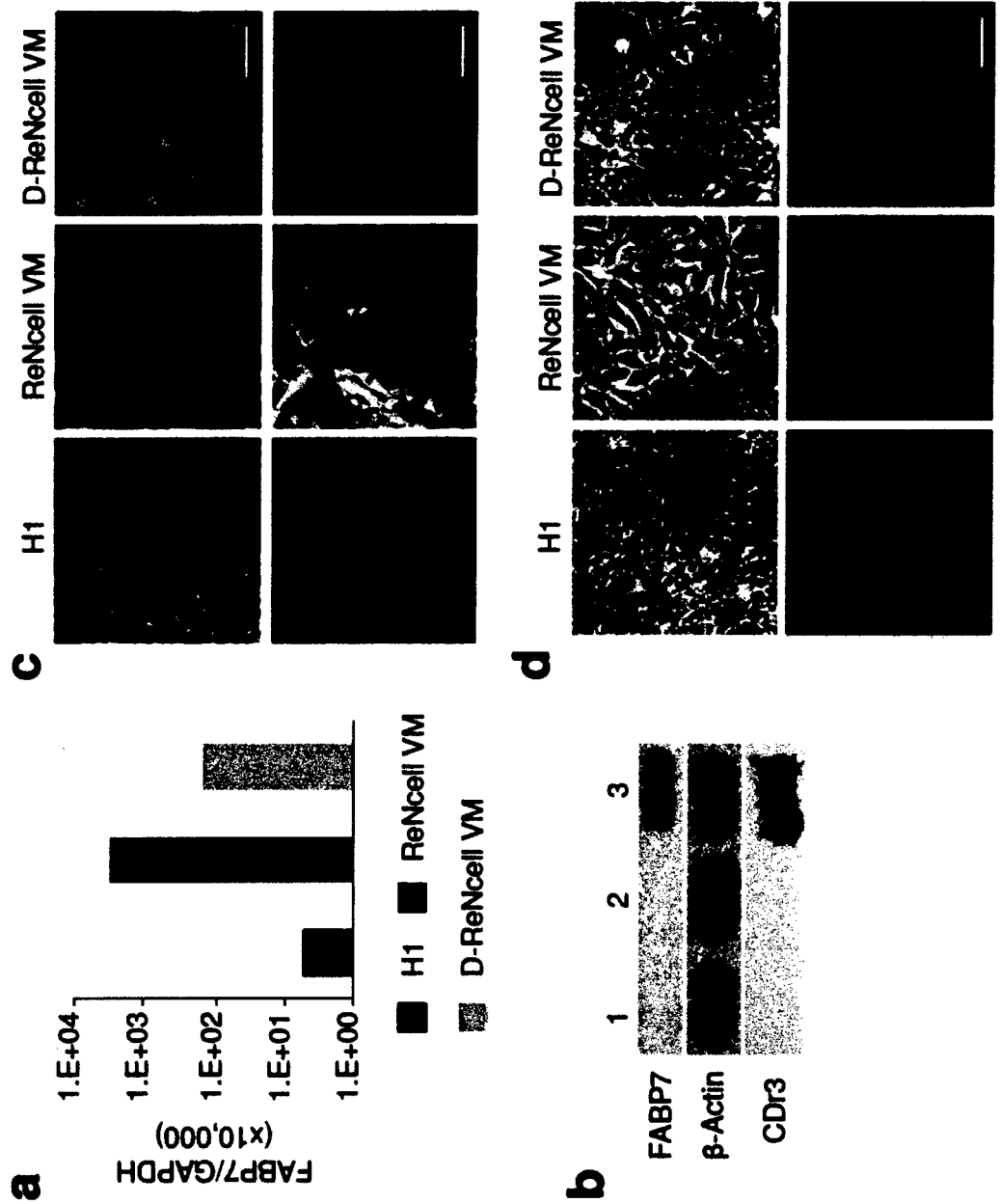
FIG. 3A shows real-time RT-PCR analysis data of FABP7 expression in H1, ReNcell VM and ReNcell VM-differentiated neurons. Relative expression level of FABP7 to GAPDH is depicted.
FIG. 3B shows that the strong signal of FABP7 protein (14 kDa) was detected by Western blotting in ReNcell VM (lane 3) lysate, while it was not detectable in the lysates of H1 (lane 1) and ReNcell VM-differentiated neurons (lane 2). β-Actin (42 kDa) staining demonstrates consistent loading across sample lanes. Fluorescence scan showed CDr3-labelled FABP7 only in the lysate of ReNcell VM (lane 3) incubated with CDr3.
FIG. 3C shows the immunocytochemistry of FABP7 in H1, ReNcell VM and ReNcell VM-differentiated neurons (D-ReNcell VM). Only ReNcell VM was brightly stained by FABP7 antibody. Scale bar, 50 μm. Upper panel, nuclei staining with DAPI; lower panel, FABP7 staining with antibody.
FIG. 3D shows H1, ReNcell VM and ReNcell VM-differentiated neurons incubated with CDr3. Fluorescence signal was detected only in ReNcell VM. Upper panel, bright field image; lower panel, fluorescence image. Scale bar, 50 μm.

With this result, we attempted to test CDr3 on a commercial ReNcell VM human NSC line derived from the ventral mesencephalon region of human foetal brain tissue. We first examined the expression level of FABP7 by real time RT-PCR and found a 540-fold higher level of FABP7 mRNA in ReNcell VM than in H1 human ESC. This expression was dramatically down-regulated (20-fold) by differentiation into neurons (FIG. 3A). Western blot analysis demonstrated a similar observation in protein expression levels with a strong FABP7 band at 14 kDa detected in ReNcell VM lysate while no FABP7 was detected in the lysates of H1 and ReNcell VM-derived neurons (FIG. 3B). In accordance with the Western blot data, ReNcell VM were strongly stained by FABP7 antibody while H1 and ReNcell VM-derived neurons were not stained (FIG. 3C). We then incubated the 3 types of cells with CDr3 to determine whether living ReNcell VM could be distinguished by the compound among others. As expected from the FABP7 expression analysis data, CDr3 selectively stained ReNcell VM in living cell cultures (FIG. 3D).

Figure 4:
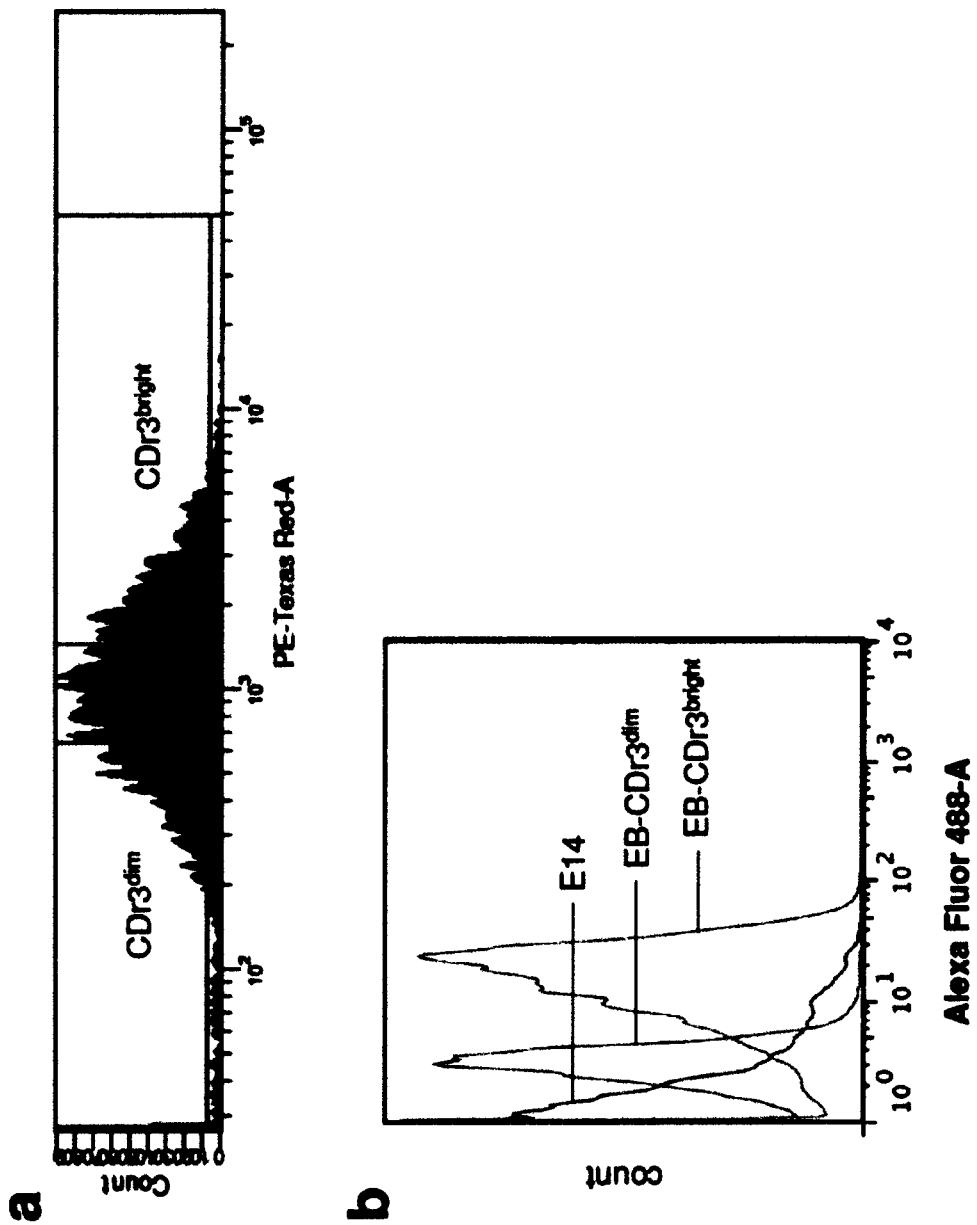
FIG. 4A shows differentiated E14 cell distribution in FACS after staining with CDr3. The CDr3-stained embryoid body cells were separated into CDr3$^{bright}$ and CDr3$^{dim}$ populations.
FIG. 4B shows the higher expression of FABP7 in CDr3$^{bright}$ than in CDr3$^{dim}$ cells, which was determined by immunocytochemistry followed by flow cytometry. The primary FABP7 antibody was detected by an Alexa Fluor 488-conjugated secondary antibody.
Figure 5:
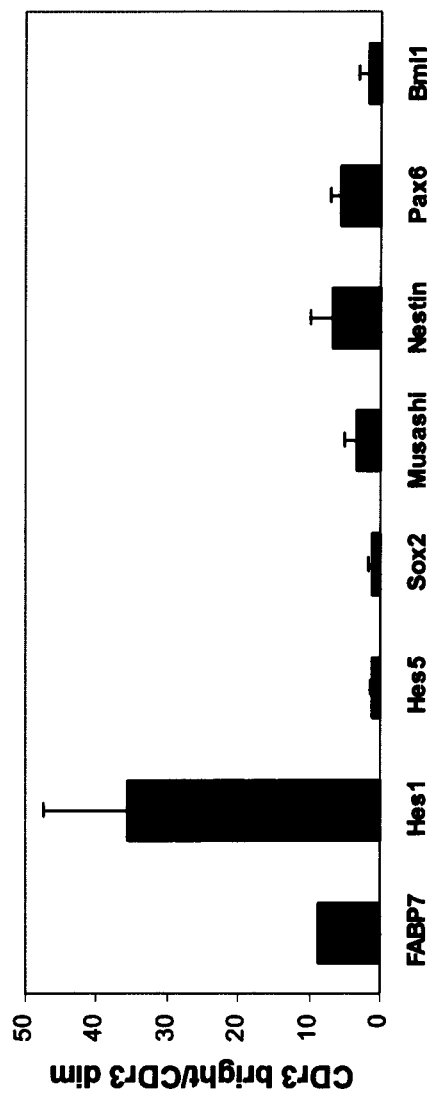
FIG. 5 shows the higher expression of FABP7, Hes1, Musashi, Nestin and Pax6 in CDr3$^{bright}$ cells than in CDr3$^{dim}$ cells. The CDr3$^{bright}$ and CDr3$^{dim}$ cells were collected separately by FACS for gene expression analysis by real time RT-PCR and neurosphere assay.
Figure 6A:
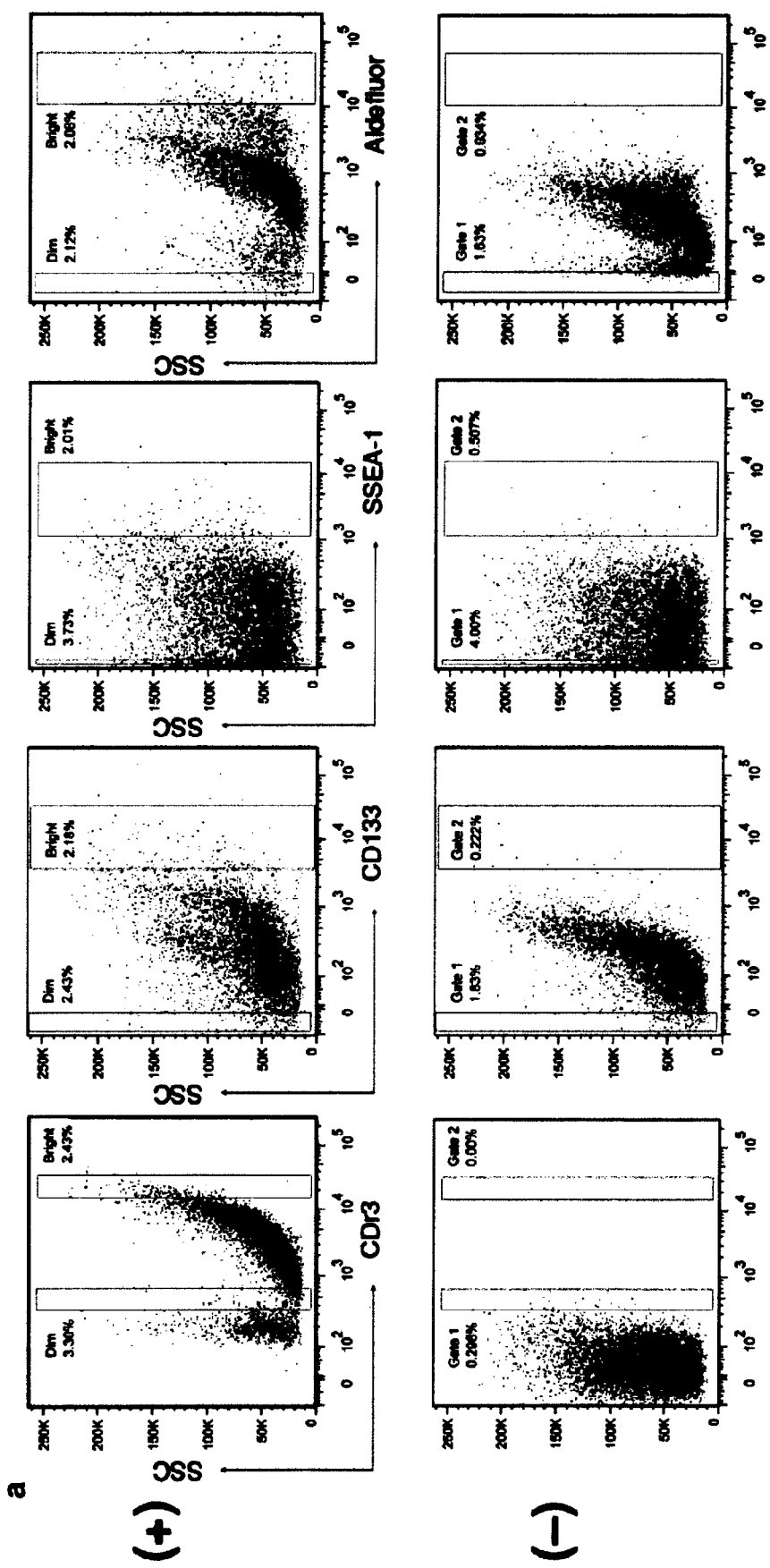
FIG. 6A shows the flow cytometry dot plot images showing shift of stained E14.5 fetal mouse brain cells to bright fluorescence (+) compared to control group (−).
Figure 6B:
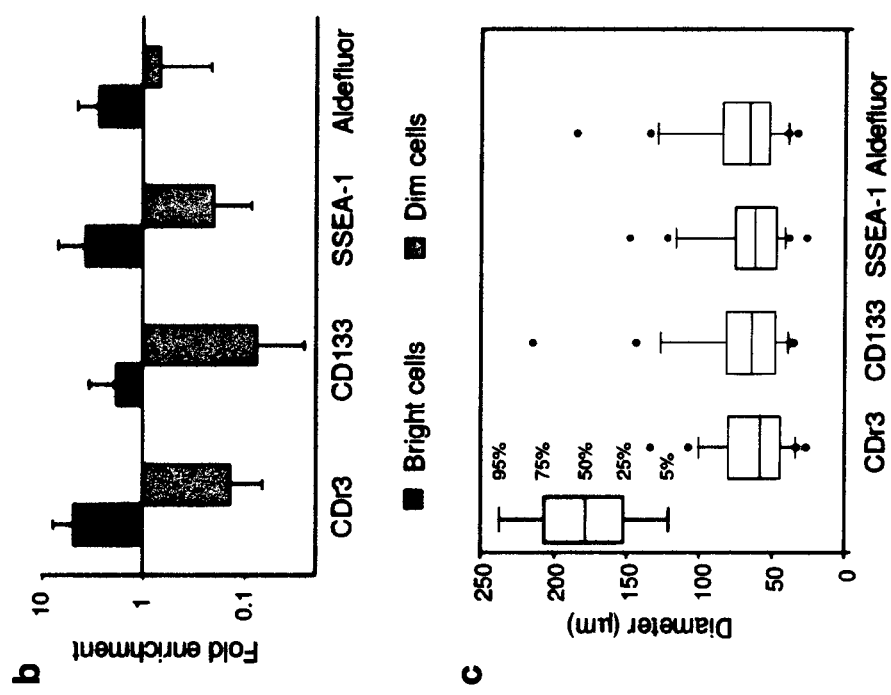
FIG. 6B shows the numbers (left panel) and the sizes (right panel) of neurospheres for the cells sorted by CDr3, CD133 antibody, SSEA-1 antibody and Aldefluor compared to unsorted cells.

Next, we were interested to test whether CDr3 can be used for the isolation of NSC from the heterogeneous populations of cells. According to the protocol described by Bibel et al.[7], we induced differentiation of E14 to generate FABP7-positive radial glial cells. The embryoid bodies generated from E14 in the absence of leukemia inhibitory factor were treated with retinoic acid for 2 days until dissociation into single cell suspension. The cells were stained with CDr3 and the CDr3bright and CDr3dim cells were collected separately by FACS. Each cell population was stained with FABP7 antibody and analyzed by flow cytometry. The overlay plot showed well-separated 2 clusters demonstrating that the cells isolated by CDr3 from the heterogeneous embryoid body cells were FABP7 expressing cells (FIG. 4). For the NSC isolation from the brain tissue, we incubated the E14.5 fetal mouse brain primary cells with CDr3, and the CDr3$^{bright}$ and CDr3$^{dim}$ cells were collected separately by FACS for gene expression analysis by real time RT-PCR and neurosphere assay. The expression levels of FABP7, Hes1, Musashi, Nestin and Pax6 in CDr3$^{bright}$ cells were more than 3-fold higher than in CDr3$^{dim}$ cells, while the differences of Hes5, Sox2 and Bmi1 expression levels were less than 2-fold (FIG. 5). In a neurosphere assay the CDr3$^{bright}$ cells grew to generate 26.8±2.5 neurospheres while CDr3$^{dim}$ cells generated only 0.25±0.5 neurospheres per well. As a separate study, we sorted the fetal mouse brain cells using CD133 antibody, SSEA-1 antibody, Aldefluor (BODIPY-aminoacetaldehyde) as well as CDr3 by FACS for neurosphere assay (FIG. 6A). We observed a big difference between all marker positive and negative cells in the numbers of generated neurospheres. Among the markers, largest number of neurospheres was generated in CDr3 positive cells followed by SSEA-1, Aldefluor and CD133 positive cells (FIG. 6B), while the sizes of neurospheres were all similar (FIG. 6C). This result shows highest correlation between neurosphere forming ability of the NSC and FABP7 level among the tested NSC markers.

Figure 7:
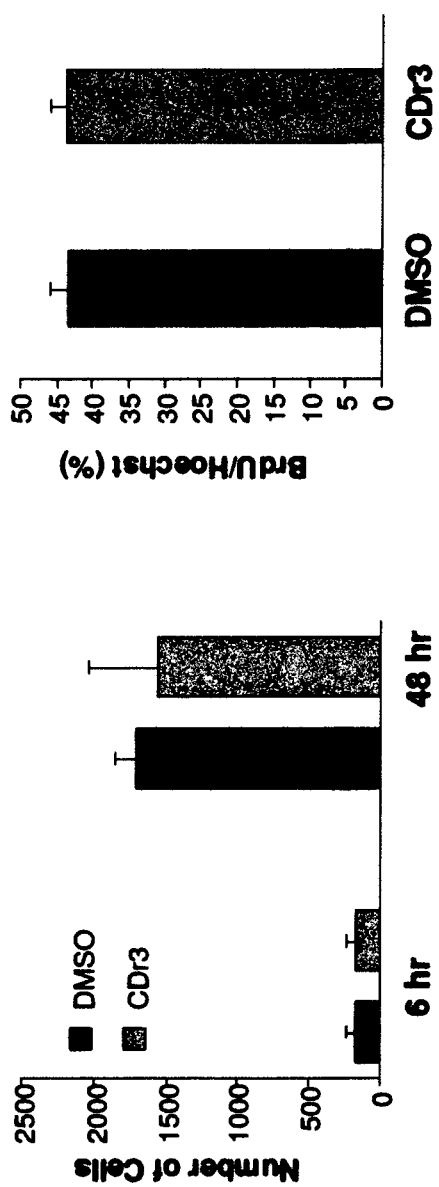
FIG. 7 shows the numbers (upper panel) and sizes (lower panel) of neurospheres cultured in the presence of CDr3 and DMSO used as a vehicle.
Figure 8:
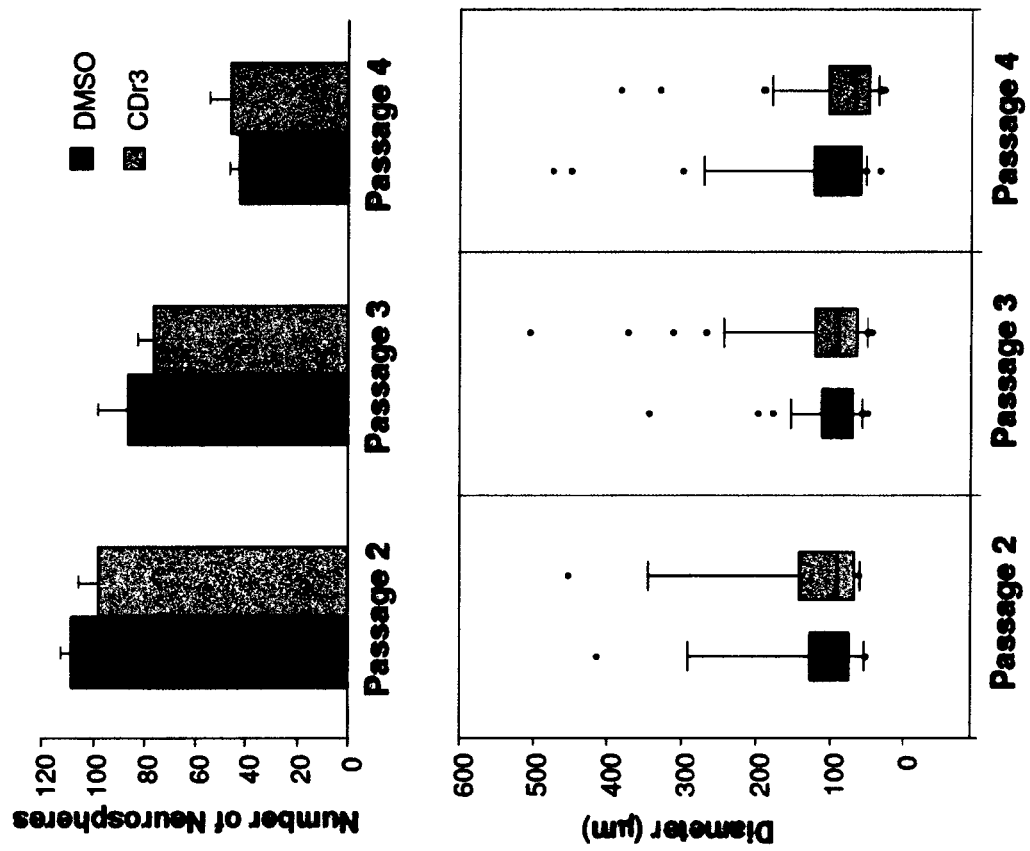
FIG. 8 shows number of NS5 cells (left panel) and percentage of BrdU-positive cells (right panel) cultured in the presence of CDr3 and DMSO used as a vehicle.

Finally, we determined whether CDr3 affects NSC proliferation by culturing NS5 and neurosphere in the presence of CDr3. Total numbers of NS5 cells grown for 6 hr and 48 hr and the percentage of BrdU positive cells pulse-labeled in the CDr3-containing medium were not different from those of cells grown in DMSO only-containing medium which was used as a control (FIG. 7). In accordance with the result of experiment with NS5 cells, the number and size of neurospheres generated in the presence of CDr3 were not different from control (FIG. 8).

Materials and Methods

Cell Culture and Differentiation

E14 was maintained on gelatin-coated dishes in high-glucose DMEM supplemented with 10% FBS, 2 mM L-glutamine, 100 U/ml penicillin, 100 µg/ml streptomycin, 0.1 mM non-essential amino acids, 0.1% β-mercaptoethanol and 100 U/ml leukemia inhibitory factor (LIF, Chemicon). For differentiation, the cells were detached from their culture plates using 0.25% trypsin with 1 mM EDTA solution (Invitrogen) and sub-cultured in non-adherent bacteria culture dishes in the E14 media but without LIF. Subsequently, 90% of the EBF media was changed on a daily basis for a total of 4 days and then retinoic acid (Sigma) was added to the final concentration of 1 µM. On day 6, the embryoid bodies were harvested and dissociated in 0.05% trypsin with 0.2 mM EDTA solution for 3 min at 37° C. to obtain a single cell suspension. NS5 was maintained in Euromed-N medium supplemented with 100 µg/ml Apo-transferin (Sigma), 5.2 ng/ml Sodium Selenite (Sigma), 19.8 ng/ml progesterone (Sigma), 16 µg/ml Putrescine (Sigma), 25 µg/ml insulin (Sigma), 50.25 µg/ml BSA (Gibco), 10 ng/ml bFGF (Gibco), 10 ng/ml EGF (Gibco), 100 U/ml penicillin (Gibco), 100 µg/ml streptomycin (Gibco) and 2 mM L-glutamine (Gibco). For differentiation of NS5 into astrocyte, the medium was changed to NS5 maintenance medium containing 5% FBS but without FGF and bEGF. MEF was maintained in the same media as used for E14 but without LIF. H1 was maintained in a feeder-free condition on matrigel-coated dishes in MEF-conditioned medium containing Knockout DMEM/10% serum replacement (Gibco), 0.1 mM MEM non-essential amino acids (Gibco), 1 mM L-glutamine (Gibco), 0.1 mM β-mercaptoethanol (Gibco), 8% plasmanate (NUH pharmacy), 12 ng/ml LIF, and 10 ng/ml human recombinant Basic Fibroblast Growth Factor (bFGF; Gibco). ReNcell VM (Millipore #SCC008) was maintained on laminin-coated dishes in ReNcell NSC Maintenance Medium (Millipore #SCM005) containing 20 ng/ml bFGF and 20 ng/m EGF. For neural differentiation, ReNcell VM were seeded on PLO/Laminin-coated plates and cultured for up to 3 weeks in media comprising a 1:1 mix of N2-DMEM/F12 and B27-Neurobasal media supplemented with 0.1 mM MEM non-essential amino acids and 1 mM L-glutamine, all obtained from Gibco/Invitrogen. For mixed primary brain cell culture, the brains of neonatal mouse pups were cut into small pieces and digested in 0.25% trypsin with 1 mM EDTA solution (Invitrogen) for 30 min at 37° C. before neutralization with FBS. After washing with PBS by centrifugation and resuspension, the tissues were triturated using a 10 ml pipette fitted with 1 ml tip and the suspension was filtered through a strainer with 40 µm nylon mesh. The obtained single cells were plated on 35 mm cell culture dishes in OptiMEM-GlutaMAX™ containing 10% FBS. Unattached cells and cell debris were removed the next day by replacing medium. One-half of the medium was replaced twice a week thereafter.

DOFL High Throughput Screening

DOFL compounds were diluted from 1 mM DMSO stock solutions with the culture medium to make final concentration of 0.5 µM or 1.0 µM. The 4 different types of cells plated side by side on 384-well plates were incubated with the compounds overnight at 37° C. and the nuclei were stained with either Hoechst33342 or DRAQ5 the next day before image acquisition. The fluorescence cell images of 2 regions per well were acquired using ImageXpress Micro™ cellular imaging system (Molecular Device) with 10× objective lens and the intensity was analyzed by MetaXpress® image processing software (Molecular Device). The hit compounds which stained NS5 more brightly than other cells were selected based on the intensity data and manual screening of the raw images.

Live Cell Staining

The cells were incubated with 0.5 µM of CDr3 in Opti-MEM GlutaMAX™ for 1 hr and, if necessary, subsequently with 2 µM of Hoechst 33342 for 15 min at 37° C. Then the cells were rinsed in the maintenance medium for 1 hr and the medium was replaced again with fresh one before image acquisition. The staining and destaining times were prolonged when necessary. The bright field and fluorescence images were acquired on ECLIPSE Ti microscope (Nikon Instruments Inc) or A1R confocal microscope (Nikon Instruments Inc) using NIS Elements 3.10 software or on Axio Observer D1 using AxioVision v 4.8 software (Carl Zeiss Inc).

Flow Cytometry and FACS

The cells incubated with CDr3 were harvested by trypsin treatment, washed and resuspended in PBS. The fluorescence intensity of the cells was measured on a flow cytometry (BD™ LSR II) or collected using a FACS machine (BD FACS Aria™). The data were analyzed and processed using FlowJo 7 software.

Two-Dimensional Gel Electrophoresis

CDr3-stained NS5 pellet was lysed in a lysis buffer (40 mM Trizma, 7M Urea, 2M thiourea and 4% CHAPS) premixed with 10 µl/ml Protease Inhibitor Cocktail (EDTA free, GE healthcare), 50 µg/ml DNase I and 50 µg/ml RNase A (Roche). The proteins of 0.2 mg and 1 mg were separated by 2DE for silver staining and fluorescent imaging, respectively. The fluorescence image of gels was acquired using a Typhoon 9400 scanner (GE healthcares) at excitation/emission wavelengths of 532 nm/610 nm with PMT at 500 v and a duplicate gel was stained using PlusOne™ Silver Staining Kit (GE healthcare) according to the manufacturer's protocol. The fluorescently 18abeled protein spots were directly excised from the gel for in-gel trypsin digestion and peptide extraction.

MALDI-TOF/TOF MS and MS/MS Analyses

Tryptic peptide of 0.6 µl was spotted onto Prespotted AnchorChip target plate (Bruker Daltonics Inc) according to manufacturer's protocol. The peptide mass fingerprint and selected peptide MS/MS fragment ion analysis were carried out on UltraFlex III TOF-TOF (Bruker Daltonics Inc) with the compass 1.2 software package including FlexControl 3.0 and FlexAnalysis 3.0 with PAC peptide calibration standards. The peak lists of MS and MS/MS were submitted to in-house Mascot server (phenyx.bii.a-star.edu.sg/search_form_select.html) through BioTools 3.2 with the database of SwissProt 57.8 (509,019 sequences) allowing peptide mass tolerance of 100 ppm and 0.5 Da with maximum 1 missed cleavage and considering variable modifications of carbamidomethyl at cysteine (C) and oxidation at methionine (M).

Chemical Synthesis

All reactions were performed in oven-dried glassware under a positive pressure of nitrogen. Unless otherwise noted, starting materials and solvents were purchased from Aldrich and Acros organics and used without further purification. Analytical TLC was carried out on Merck 60 F254 silica gel plate (0.25 mm layer thickness) and visualization was done with UV light. Column chromatography was performed on Merck 60 silica gel (230-400 mesh). NMR spectra were recorded on a Bruker Avance 300 NMR spectrometer. Chemical shifts are reported as δ in units of parts per million (ppm) and coupling constants are reported as a J value in Hertz (Hz). Mass of all the compounds was determined by LC-MS of Agilent Technologies with an electrospray ionization source. All fluorescence assays were performed with a Gemini XS fluorescence plate reader.

Synthesis of compound 1: The intermediate 1 in the Scheme 1 was synthesized as reported previously[8].

Synthesis of CDr3: 1, (20 mg, 0.047 mM) and 3,4-dimethoxybenzaldehyde (16 mg, 0.094 mM) were dissolved in acetonitrile (4 ml), followed by the addition of the mixture of pyrrolidine (23.6 μl, 0.282 mM) and acetic acid (16.1 μl, 0.282 mM). The reaction was heated at 85° C. for 15 min and then cooled down to r.t. The resulting crude mixture was concentrated under vacuum and purified by normal-phase column chromatography (eluting system: hexane/ethyl acetate (6:1) to render CDr3 as purple solid (15 mg, 56% yield).

Characteristics of CDr3
1H and 13C NMR Spectra on CDr3

1H NMR (300 MHz, CDCl3): 2.28 (s, 3H), 2.96 (t, J=7.5 Hz, 2H), 3.40 (t, J=7.5 Hz, 2H), 3.92 (s, 3H), 3.97 (s, 3H), 4.78 (s, 2H), 6.30 (d, J=3.9 Hz, 1H), 6.71 (s, 1H), 6.85 (d, J=3.9 Hz, 1H), 6.86 (d, J=8.1 Hz, 1H), 7.03 (s, 1H), 7.12 (d, J=1.8 Hz, 1H), 7.16 (dd, J=1.8, 8.4 Hz, 1H), 7.29 (d, J=16.2 Hz, 1H), 7.48 (d, J=16.2 Hz, 1H).

13C NMR (75.5 MHz, CDCl3): 11.3, 23.7, 29.6, 33.0, 55.9, 56.0, 56.1, 74.0, 94.9, 109.6, 110.4, 111.1, 116.2, 116.6, 121.6, 122.1, 122.2, 126.7, 129.2, 133.6, 139.1, 143.0, 149.3, 150.8, 171.0.

ESI-MS m/z ($C_{25}H_{24}BCl_3F_2N_2O_4$) calculated: 571.1 (M+H)+. found: 551.1 (M−F).

Fluorescence Property Measurement

Figure 9:
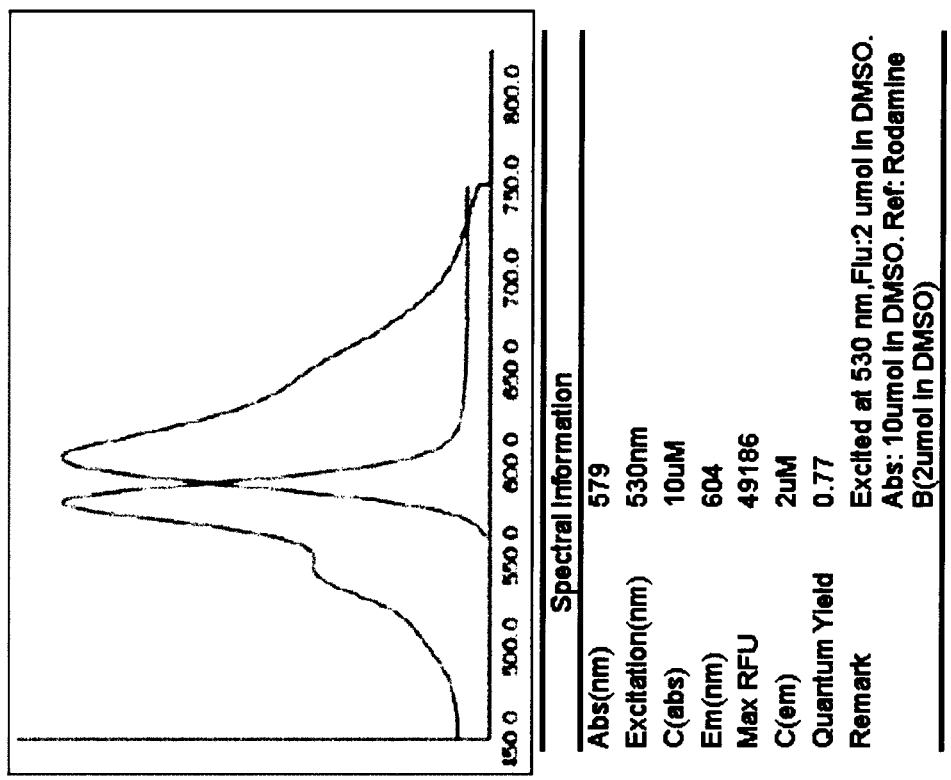
FIG. 9 shows the spectroscopic information of CDr3.

10 μM solutions in DMSO was prepared and measured absorption and 2 μM solutions in DMSO was prepared and measured absorption emission of library compound. Spectrum of CDr3 is shown in FIG. 9.

Neural Stem Cell Isolation from Fetal Mouse Brain Cell Suspension

E14.5 fetal mouse brains were trypsinized in 0.25% trypsin with 1 mM EDTA solution (Invitrogen) for 30 mins at 37° C. before neutralization with FBS. The tissues were triturated sequentially with a 10 ml pipette followed by a 1 ml blue tip and a 0.2 ml yellow tip attached to the 10 ml pipette until the cell suspension flows through smoothly. The tissue suspension was washed 3 times with PBS by repeated resuspension and centrifugation and filtered through a 40 μm strainer. The cells were stained using CDr3, CD133 antibody, SSEA-1 antibody or Aldefluor as described below and FACS sorted. The FACS sorted bright and dim cells of 2% at each end and unsorted (randomly harvested) cells were plated in a DMEM/F12 medium containing 10 ng/ml bFGF, 20 ng/ml EGF and B27 without vitamin A (Invitrogen) at a density of 10,000 cells/well in 6-well plate to grow forming spheres. The number and size of neurospheres generated from each group were measured after 6 days culture.

CDr3

Dissociated cells were incubated with 0.5 μM of CDr3 in neurosphere media for 1 hr and then spun down for resuspension in compound free neuropshere media for 30 minutes. The cells were then spun down and resuspended in PBS for FACS. For control group, the cells were incubated with 0.05% DMSO instead of CDr3.

CD133 Antibody

Dissociated cells were blocked in 1% BSA for 30 min and then incubated with CD133 antibody (1:500) for 1 hr. The cells were washed with PBS by centrifugation and resuspension and then incubated with Alexa fluor 488-conjugated anti-rat IgG (1:1,000) for 1 hr. The stained cell sample was washed again before resuspension in PBS for FACS. For control group, primary antibody was omitted.

SSEA-1 Antibody

Dissociated cells were blocked in 1% BSA for 30 min and then incubated with SSEA-1 antibody (1:500) for 1 hr. The cells were washed with PBS by centrifugation and resuspension and then incubated with Alexa fluor 633-conjugated anti-mouse IgM (Invitrogen) for 1 hr. The stained cell sample was washed again before resuspension in PBS for FACS. For control group, primary antibody was omitted.

Aldefluor

The cells were incubated with activated Aldefluor substrate (5 μl/ml) for 30 min at 37° C. The cells were then spun down and resuspended in Aldefluore assay buffer for FACS. For control, diethylaminobenzaldehyde, a specific inhibitor of ALDH was added (5 μl/ml) to the cells together with Aldefluore substrate.

Serial Neurosphere Assay

Neurospheres were generated from the fetal mouse brain cells prepared as described in above (Neural stem cell isolation). After expansion by 2 times of passages, the cells plated in triplicate in 6-well culture plates at a density of 3,000 cells per well and cultured in the presence of 1 μM CDr3 or 0.1% DMSO for 6 days. After 6 days, the numbers and sizes of neurospheres were determined. For serial assay, the neurospheres were further passaged in the medium containing 1 μM CDr3 or 0.1% DMSO.

NS5 Cell Proliferation Assay

NS5 were seeded into 96-well plates (Greiner) at a density of 1000 cells/well. The next day, DMSO and 1 mM DMSO stock of CDr3 was added into 32 wells for each to be diluted to 0.1% and 1 uM, respectively. At 6 hr and 48 hr time points, 1 ug/ml of Hoechst 33342 was added and incubated for 15 min for image acquisition using an ImageXpress Micro™ and MetaXpress Imaging system (Molecular Devices). Hoeschst33342 and CDr3 signals were detected via DAPI and Texas red filters, respectively, and the images of a total of 4 areas were captured per well. Multi wavelength scoring analysis was then run to quantify the number of cells based on Hoechst 33342-stained nuclei image. For the quantification of pulse-labeled cells with BrdU, the cells were stained using FITC conjugated anti-BrdU antibody (BD Pharmingen™) according to the manufacturer's instruction. Total numbers of Hoechst 33342-stained and BrdU-labeled nuclei were counted by image based analysis using ImageJ-ITCN software.

REFERENCES 1. (a) Geddes, C. D.; Lakowicz, J. R. Topics in Fluorescence Spectroscopy, Vol. 9; Springer: New York, 2005. (b) Geddes, C. D.; Lakowicz, J. R. Topics in Fluorescence *Spectroscopy, Vol.* 10; Springer: New York, 2005.
2. Okano, H. & Sawamoto, K. Neural stem cells: involvement in adult neurogenesis and CNS repair. *Philos Trans R Soc Lond B Biol Sci* 363, 2111-22 (2008).

3. Falk, S. & Sommer, L. Stage- and area-specific control of stem cells in the developing nervous system. *Curr Opin Genet Dev* 19, 454-60 (2009).
4. Shimazaki, T. Biology and clinical application of neural stem cells. *Horm Res* 60 Suppl 3, 1-9 (2003).
5. Daadi, M. M., et al. Adherent self-renewable human embryonic stem cell-derived neural stem cell line: functional engraftment in experimental stroke model. *PLoS One* 3, e1644 (2008).
6. Malatesta, P., et al. Isolation of radial glial cells by fluorescent-activated cell sorting reveals a neuronal lineage. *Development* 127, 5253-63 (2000).
7. Bibel, M. et al. Differentiation of mouse embryonic stem cells into a defined neuronal lineage. *Nat Neurosci* 7, 1003-9 (2004).
8. Malan, S. F. et al. Fluorescent ligands for the histamine H2 receptor: synthesis and preliminary characterization. *Bioorg Med Chem* 12, 6495-503 (2004).

While this invention has been particularly shown and described with references to example embodiments thereof, it Will be understood by those skilled in the art that various changes in form and details may be made therein without departing from the scope of the invention encompassed by the appended claims.

$C_6$)alkyl, hydroxy($C_0$-$C_6$)alkyl, ($C_6$-$C_{10}$)aryl, halo($C_6$-$C_{10}$)aryl, hydroxy($C_6$-$C_{10}$)aryl, ($C_1$-$C_6$)alkoxy, halo ($C_1$-$C_6$)alkoxy, ($C_3$-$C_8$)cycloalkyl, halo($C_6$-$C_{10}$)aryl ($C_1$-$C_6$)alkoxy, halogen, amino, ($C_1$-$C_6$)alkoxy($C_6$-$C_{10}$) aryl($C_1$-$C_6$)alkoxy, nitro, (3 to 9 membered) heterocyclyl, ($C_0$-$C_6$)alkyl($C_6$-$C_{10}$)aryl($C_0$-$C_6$)alkoxy, ($C_5$-$C_{10}$)heterocycle, —$OCF_3$, —$B(OH)_2$, cyano($C_1$-$C_6$)alkylene amino, ($C_1$-$C_6$)alkoxyamino, ($C_6$-$C_{10}$)aryl ($C_2$-$C_6$)alkenyl, ($C_2$-$C_6$)alkenyl($C_1$-$C_6$)alkoxy, ($C_1$-$C_6$) sulfoxy or —$N(CH_3)(C_1$-$C_6)OH$.

2. The compound of claim 1, wherein:
R is ($C_5$-$C_{10}$)heteroaryl, optionally substituted with 1-4 substituents independently selected from ($C_5$-$C_{10}$)heteroaryl, ($C_6$-$C_{10}$)aryl, halo($C_6$-$C_{10}$)aryl, ($C_1$-$C_6$)alkoxy, ($C_1$-$C_6$)alkyl, halo($C_1$-$C_6$)alky, hydroxy($C_0$-$C_6$)alkyl, or
($C_0$-$C_6$)alkoxy($C_6$-$C_{10}$)aryl.

3. The composition of claim 1, wherein R is aryl.
4. The compound of claim 3, wherein R is phenyl.
5. The compound of claim 4, wherein R is optionally substituted with 1-4 ($C_1$-$C_6$)alkoxy substituents.

What is claimed is:
1. A compound represented by structural Formula (I) or pharmaceutically acceptable salts thereof:

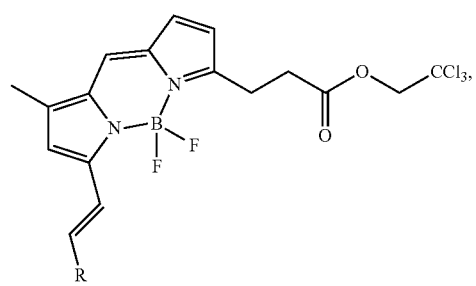

(Formula I)

wherein:
R is ($C_6$-$C_{10}$)aryl, ($C_5$-$C_{10}$)heteroaryl, ($C_6$-$C_{10}$)aryl($C_2$-$C_6$)alkenyl or 2-4 member polycyclyl, wherein each 2-4 member polycyclyl optionally and independently contains 1-2 ring heteroatoms selected from oxygen, nitrogen and sulfur;
and wherein R is optionally substituted with 1-4 substituents independently selected from ($C_1$-$C_6$)alkyl, halo($C_1$-

6. The compound of claim 4, wherein the compound is represented by structural Formula (II):

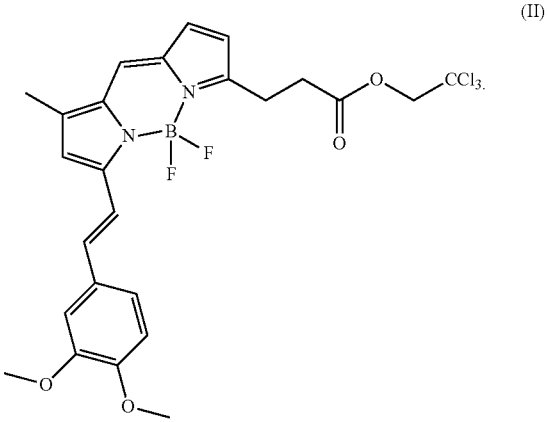

(II)

7. A method for detection of a neural stem cell (NSC), comprising:
a) staining said neural stem cell with a compound, forming a dye-stained neural stem cell by binding said compound to a marker protein of said neural stem cell, wherein said compound is of structural Formula (I) or pharmaceutically acceptable salts thereof:

(Formula I)

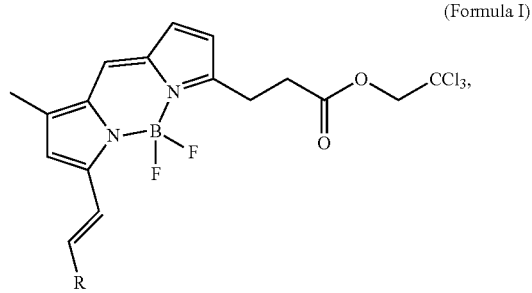

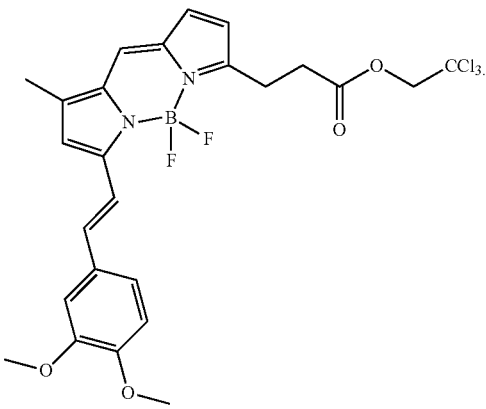

wherein:
R is $(C_6-C_{10})$aryl, $(C_5-C_{10})$heteroaryl, $(C_6-C_{10})$aryl$(C_2-C_6)$alkenyl or 2-4 member polycyclyl, wherein each 2-4 member polycyclyl optionally and independently contains 1-2 ring heteroatoms selected from oxygen, nitrogen and sulfur;

and wherein R is optionally substituted with 1-4 substituents independently selected from $(C_1-C_6)$alkyl, halo$(C_1-C_6)$alkyl, hydroxy$(C_0-C_6)$alkyl, $(C_6-C_{10})$aryl, halo$(C_6-C_{10})$aryl, hydroxy$(C_6-C_{10})$aryl, $(C_1-C_6)$alkoxy, halo$(C_1-C_6)$alkoxy, $(C_3-C_8)$cycloalkyl, halo$(C_6-C_{10})$aryl$(C_1-C_6)$alkoxy, halogen, amino, $(C_1-C_6)$alkoxy$(C_6-C_{10})$aryl$(C_1-C_6)$alkoxy, nitro, (3 to 9 membered) heterocyclyl, $(C_0-C_6)$alkyl$(C_6-C_{10})$aryl$(C_0-C_6)$alkoxy, $(C_5-C_{10})$heterocycle, —OCF$_3$, —B(OH)$_2$, cyano$(C_1-C_6)$alkylene amino, $(C_1-C_6)$alkoxyamino, $(C_6-C_{10})$aryl$(C_2-C_6)$alkenyl, $(C_2-C_6)$alkenyl$(C_1-C_6)$alkoxy, $(C_1-C_6)$sulfoxy or —N(CH$_3$)(C$_1$-C$_6$)OH;

b) incubating product of step a) to form a said incubated dye-stained stem;

c) analyzing said incubated dye-stained stem cell by a flow cytometry and FACS; and d) subjecting said dye-stained neural stem cell to two-dimensional SDS-PAGE (2DE) fluorescence scanning to detect fluorescence signal, wherein the presence of a signal is indicative of the presence of said neural stem cell.

8. The method of claim 7, wherein:
R is $(C_5-C_{10})$heteroaryl optionally substituted with 1-4 substituents independently selected from $(C_5-C_{10})$heteroaryl, $(C_6-C_{10})$aryl, halo$(C_6-C_{10})$aryl, $(C_1-C_6)$alkoxy, $(C_1-C_6)$alkyl, halo$(C_1-C_6)$alky, hydroxy$(C_0-C_6)$alkyl, or $(C_0-C_6)$alkoxy$(C_6-C_{10})$aryl.

9. The method of claim 7, wherein R is aryl.

10. The method of claim 9, wherein R is phenyl.

11. The method of claim 10 wherein R is optionally substituted with 1-4 $(C_1-C_6)$alkoxy substituents.

12. The method of claim 11, wherein the compound is represented by structural Formula (II):

13. The method of claim 7, wherein said neural stem cell is a human or a mouse neural stem cell.

14. The method of claim 7, wherein said marker protein is a fatty acid binding protein 7 (FABP7).

15. The compound of claim 1, wherein the compound is represented by structural Formula (III):

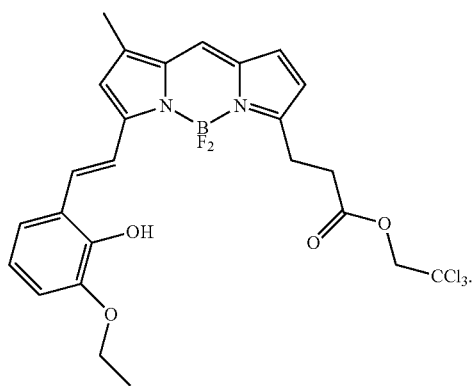

16. A compound represented by Formula (IV), or pharmaceutically acceptable salts thereof:

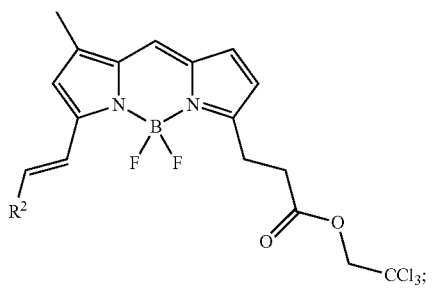

wherein R$^2$ is $(C_4-C_{12})$heteroaryl, optionally substituted with 1-4 substituents independently selected from $(C_1-C_6)$alkyl, $(C_6-C_{10})$aryl, $(C_1-C_6)$hydroxyalkyl, or $C_4-C_{12}$)heteroaryl, wherein $(C_6-C_{10})$aryl is optionally substituted with one or more substituents selected from halo or $(C_1-C_6)$alkoxy.

17. The compound of claim 16, wherein the compound is represented by structural Formula (V):
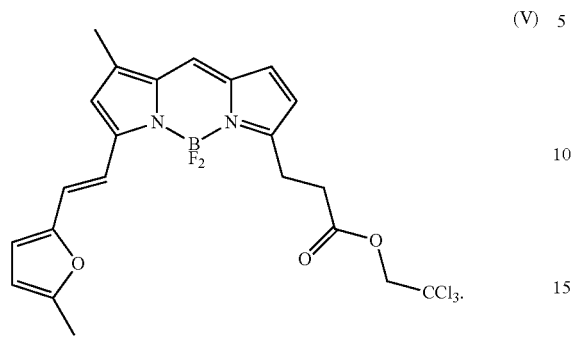
(V)